US012741033B2

(12) United States Patent
Butzloff

(10) Patent No.: US 12,741,033 B2
(45) Date of Patent: Sep. 22, 2026

(54) NOOTROPIC FULLERENES AND USE

(71) Applicant: CARBON 60 (ZHEJIANG) PHARMACEUTICAL TECHNOLOGY CO., LTD., Hangzhou (CN)

(72) Inventor: Peter Butzloff, Walnut, CA (US)

(73) Assignee: CARBON 60 (ZHEJIANG) PHARMACEUTICAL TECHNOLOGY CO., LTD., Hangzhou (CN)

( * ) Notice: Subject to any disclaimer, the term of this patent is extended or adjusted under 35 U.S.C. 154(b) by 870 days.

(21) Appl. No.: 17/674,512

(22) Filed: Feb. 17, 2022

(65) Prior Publication Data

US 2022/0193257 A1 Jun. 23, 2022

Related U.S. Application Data

(63) Continuation-in-part of application No. PCT/US2020/046027, filed on Aug. 12, 2020, and a continuation-in-part of application No. 17/579,967, filed on Jan. 20, 2022, and a continuation-in-part of application No. 17/581,465, filed on Jan. 21, 2022, now abandoned, said application No. 17/579,967 is a continuation of application No. PCT/US2021/062908, filed on Dec. 10, 2021, said application No. 17/581,465 is a continuation-in-part of application No. PCT/US2021/063977, filed on Dec. 17, 2021, and a continuation of application No. PCT/US2021/062908, filed on Dec. 10, 2021.

(60) Provisional application No. 63/154,899, filed on Mar. 1, 2021.

(51) Int. Cl.

| | |
|---|---|
| ***C07F 15/00*** | (2006.01) |
| ***A61K 31/7076*** | (2006.01) |
| ***A61K 38/06*** | (2006.01) |
| ***A61K 47/69*** | (2017.01) |

(52) U.S. Cl.
CPC ...... *A61K 47/6949* (2017.08); *A61K 31/7076* (2013.01); *A61K 38/063* (2013.01)

(58) Field of Classification Search
CPC ................................ A61K 38/063; A61K 9/51
See application file for complete search history.

(56) References Cited

U.S. PATENT DOCUMENTS

| | | |
|---|---|---|
| 5,364,993 A | 11/1994 | Zhang et al. |
| 2008/0206222 A1 | 8/2008 | Miwa et al. |
| 2009/0012008 A1 | 1/2009 | Laptev et al. |
| 2010/0144868 A1 | 6/2010 | Gozin et al. |
| 2012/0080305 A1 | 4/2012 | Koruga |
| 2014/0044690 A1 | 2/2014 | Chen et al. |
| 2018/0243250 A1 | 8/2018 | Bolsöy |
| 2018/0297928 A1 | 10/2018 | Dugan et al. |
| 2019/0053991 A1 | 2/2019 | Krishna et al. |
| 2022/0273804 A1 | 9/2022 | Butzloff |
| 2022/0273814 A1 | 9/2022 | Butzloff |
| 2024/0091376 A1 | 3/2024 | Butzloff |

FOREIGN PATENT DOCUMENTS

| | | |
|---|---|---|
| CN | 102503879 A | 6/2012 |
| CN | 108084451 A | 5/2018 |
| CN | 108079019 B | 4/2020 |
| CN | 112335521 A | 2/2021 |
| WO | 2004/067678 A1 | 8/2004 |
| WO | 2012/054936 A1 | 4/2012 |
| WO | 2019/117986 A1 | 6/2019 |
| WO | 2020/068817 A1 | 4/2020 |
| WO | 2020/257064 A1 | 12/2020 |
| WO | 2021/162725 A1 | 8/2021 |
| WO | 2022/035429 A1 | 2/2022 |

OTHER PUBLICATIONS

Alsulam et al., High-Yield Continuous-Flow Synthesis of Spheroidal C60@Graphene Composites as Supercapacitors. ACS Omega. Nov. 7, 2019;4(21): 19279-19286.
Bjelakovic et al., Design, synthesis, and characterization of fullerene-peptide-steroid covalent hybrids. Tetrahedron. Nov. 11, 2014;70(45):8564-8570.
Choukekar et al., Parkinson's Disease: An Overview of Various Tratments. International Journal of Research and Review. Dec. 2020;7(12):383-399.
Frazao et al., Four-level levodopa adsorption of C60 fullerene for transdermal and oral administration: a computational study. RSC Advances. 2012;2(22): 8306-8322, pre-publication edition.
Kumar et al., Alzheimer Disease. Study Guide from StatPearls Publishing. 9 pages, May 16, 2018.
O'Gorman Tuura et al., Beyond Dopamine: GABA, Glutamate, and the Axial Symptoms of Parkinson Disease. Front Neurol. Sep. 26, 2018;9:806, 9 pages.

(Continued)

*Primary Examiner* — James W Rogers
(74) *Attorney, Agent, or Firm* — McCarter & English, LLP; Wei Song

(57) ABSTRACT

A dual neurotransmitter nanoparticle composition is provided to store and transport protons and cations across neural cell membranes. This composition mitigates cognitive deficits in neurological pathologies such as autism spectrum disorder and some symptoms of Alzheimer's disease, as well as to reduce the severity of aging related reactive oxygen species damage in ASD and AD brains that are caused by bioenergetic dysfunction. The antioxidant and protein oligomer disassembly properties can also be used to alleviate corneal cataracts. The composition comprises C60 fullerenes bonded to one glutathione molecule and one or more molecules of adenosine triphosphate and can be produced at low temperatures through reactive shear mixing. This composition therapeutically improves and prophylactically preserves cognitive performance, memory, and mental acuity to alleviate deficits arising from bio-electrochemical dysfunction in brain cells.

16 Claims, 25 Drawing Sheets

(56) References Cited

Sun et al., A Novel Strategy for Treating Inflammatory Bowel Disease by Targeting Delivery of Methotrexate through Glucan Particles. Adv Healthcare Mater. 2020;9:1901805, 13 pages.
Zheng et al., Exploitation of unique properties of zeolites in the development of gas sensors. Sensors (Basel). 2012;12(4):5170-94.
International Search Report and Written Opinion for Application No. PCT/US2021/063977, dated May 5, 2022, 12 pages.
International Search Report and Written Opinion for Application No. PCT/US2021/062908, dated Apr. 27, 2022, 10 pages.
International Search Report and Written Opinion for Application No. PCT/US2020/046027, dated Nov. 6, 2020, 6 pages.
International Search Report and Written Opinion for Application No. PCT/US2022/017589, dated May 16, 2022, 11 pages.
International Search Report and Written Opinion for Application No. PCT/US2022/019857, dated Jun. 8, 2022, 8 pages.

140
130
O
P
NaO
O (-) Na(+)
ONa

NOOTROPIC FULLERENES AND USE

CROSS-REFERENCE TO RELATED APPLICATIONS

This application is a continuation-in-part of international application PCT/US20/46027 filed on Aug. 12, 2020 and also a continuation-in-part of U.S. patent application Ser. No. 17/579,967 filed on Jan. 20, 2022, and also a continuation-in-part of U.S. patent application Ser. No. 17/581,465 filed on Jan. 21, 2022; U.S. patent application Ser. No. 17/579,967 is a continuation of international application No. PCT/US21/62908 filed on Dec. 10, 2021 and also claims the benefit of U.S. provisional patent application No. 63/154,899 filed Mar. 1, 2021; U.S. patent application Ser. No. 17/581,465 claims priority to U.S. provisional patent application No. 63/154,899 and is a continuation-in-part of international application No. PCT/US21/623977 filed Dec. 17, 2021, and also a continuation of international application No. PCT/US2021/062908, which also claims the benefit of U.S. provisional patent application No. 63/154,899. Each of the aforementioned applications is incorporated by reference herein in its entirety.

BACKGROUND OF THE INVENTION

Field of the Invention

The invention is directed in general to a composition of matter to improve biochemical REDOX homeostasis and bioenergetic neural electrochemistry using the dual neurotransmitters of glutathione (GSH) and adenosine triphosphate (ATP) which are derivatized onto buckminsterfullerene (C60). Methods of use to prevent or to treat autism spectrum disorder (ASD), some symptoms of Alzheimer's Disease, and related neurocognitive deficits are provided. Other provided methods include eyedrops as one method to deliver C60-GSH-ATP to treat ASD, eyedrops to treat the formation of cataracts or opacity of the ocular cornea, or for use as a topical skin protection from sunlight. Delivery methods include ingestion, inhalation, or injection when used as a medicament or as a food supplement to maintain or re-establish benign healthy neural cellular homeostasis.

DESCRIPTION OF THE PRIOR ART

The multiple neurodevelopmental features of autism spectrum disorder become apparent in children and persist over the lifetime, slowing the rate of brain maturation and altering the neural processing of the brain in individuals at all levels of intelligence. ASD is genetic and has diverse features that are heritable and complexly distributed over all chromosomes. Sometimes ASD can act to promote obsessive learning behaviors that favor attention to detail in the learning process to apparent extraordinary benefit, as was likely the case for individuals of historical importance to the advancement of scientific knowledge such as Charles Darwin. More often, these deficits lead to obsessive compulsion disorders that decrease both social interaction ability and can detrimentally impact long term survival or quality of life for the affected people as well as their care takers and family members. ASD is characterized by reduced interest in, or apparent inability to learn, effective social communication. The high focus level on task, while potentially beneficial in some contexts, is undesirable when a change in a task or multi-tasking is needed to address real world demands on time and resources. The origin of inflexibility on tasks is thought to arise from the need to amplify insufficiently strong neural input, leading to hypersensitivity to noise, light, and too much information. When enough overload of mental processes is present, this results in a need to dismiss the extraneous signal interference and is likely the origin of lessened social interaction. Another equally important aspect of this need to constantly focus attention, is the loss of a proper sense of time, as the passing of hours is dismissed as irrelevant information, thereby leading to sleep disorders and poor fatigue recovery.

Biochemically, autism is often associated with increased reactive oxygen species (ROS) in neurons but separating out the origin of these stressors from a spectrum of genetic changes from the norm, as compared to poor sleep states, has been confounded by the behavior and sleep deprivation that is common in autism. In any case, the effects of surface charges in contact with the cell cytosol, proteins, and the lipid membranes of the endoplasmic reticulum become insufficiently engaged in these interactions. This autism related deficit, along with ROS associated in the aging process, are thought to contribute to mitochondrial stress. In particular, these stressors are related to an imbalance of the reduction-oxidation process (REDOX) of the electron transfer cycle that allows cellular respiration to take place, and the result can be the production of misfolded proteins that are associated with many kinds of mental deficits and neuro-physiological pathologies.

The highest specialization of animals is neural tissue, where neurons have the greatest need for energy, and therefore also obtain the highest concentration of energy harvesting mitochondria in their structures. The brains of higher organisms have evolved strategies to significantly reduce neural size to fit more computational capacity into the same volume. The human brain weight is about 2% of body weight, yet it needs 20% of the total oxygen consumption, and consumes approximately 25% of total body glucose utilized by oxidation to produce energy and release carbon dioxide and water in that process.

A delicate chemical balance of reduction and oxidation (REDOX) operates mitochondria and drives cellular function, especially neural function, which is the most energy intensive and therefore the most reliant on mitochondria for energy. Proper brain function can become compromised when genetically encoded or environmentally induced misdevelopment or evolutionary induced miniaturization of neural structures become compromised by cellular respiration related energy deficits. Autism is impacted by mitochondrial dysfunction in multiple ways. Neural cell migration in the developing brain may have resulted in unusual or poor cortical layer differentiation. The remodeling of dendritic spines is also compromised in autistic brains and may result in the loss of learning plasticity. It is verified at this point, that the level of neural electrical signals is attenuated in voltage and reduced in signal strength in the brains of autistic people.

Deficits or dysfunction in metabolic REDOX control, likely originating either with oxidative stress or reductive stress, is implicated in origin of mental deficits and cognitive malfunction in autism spectrum disorders as well as in the natural aging process. However, there is no specific treatment or therapy for mitochondrial dysfunction.

Both the aging process and the autism spectrum disorders have complex etiologies, yet it is of significant interest that they seem to share a dysfunctional mechanism of REDOX pathology, leading to the production of reactive oxygen species in cellular mitochondria. The release of ROS by mitochondria is characterized by hydrogen peroxide ($H_2O_2$), and a wide variety of biological molecules involved with REDOX control. Both in aging and in autism, NADPH levels are decreased, resulting in the reduced concentration of its precursor, nicotinamide adenine dinucleotide (NAD+). This leads to increased levels of the ratio of [NADP+]/[NADPH], leading to a cascade of pathological effects. These effects include increases in oxidative stress, mitochondrial electron transport chain dysfunction, and the promotion of inflammation in brain tissues.

Impairment of mitochondrial metabolism and defective mitophagy results in age associated neurodegeneration. The fact that neuronal cells are more vulnerable to degeneration in several pathological conditions, including Parkinson's disease, amyotrophic lateral sclerosis (ALS) and Charcot-Marie-Tooth disease, underlines the urgent need for redundant mechanisms to regulate the removal of defective mitochondria, or in the case of autism, to establish conditions leading to a normal immune response that allows proper mitophagy.

Convergent evidence in the field of neuroscience supports a model where mitochondrial homeostasis is tightly associated with synaptic activity and neural plasticity. Synapses are highly vulnerable to oxidative and proteotoxic stress, leading to accumulation of protein aggregates and dysfunctional organelles, especially in the region of mitochondrial associated membranes.

The role of mitophagy in synaptic homeostasis is a relatively new field in neuroscience. There is no effective medication against psychiatric and neurodegenerative pathologies. Therefore, the development of novel therapeutic strategies to modulate synaptic mitophagy and electrochemical exchange at or between neural organelles could confer neuroprotection and either prevent synapse pathology before irreversible brain damage, or even reverse some of these effects.

Modern research confirms that the neurons of autistic brains respond with less electrical activity than controls when electric currents are deliberately blocked and then restarted, especially those of the pyramidal neurons in the outer layer of the neocortex, designated as layer CA1. This suggests autistic neurons have lost their ability to adjust the current flowing through them. The treatment with lithium ions temporarily restores pyramidal cell ability to reduce excitatory firing rates and build up more current before releasing voltage spikes, which is an encouraging result, but it remains unclear whether the simplistic lithium ion substitution acts directly on a dysregulated autism gene, SHANK3 or on some other target in the neural circuit. Lithium is not a part of the normal diet, and it is an extraneous ionic conductor to the normal human biological ion exchange processes. A significant enhancement of cognitive ability in the long term has not been demonstrated by the action of lithium. Both more research and a more sophisticated neural circuit remodeling design concept are likely required to fully correct a wide spectrum of autistic neural deficits.

Autism spectrum disorder is more highly correlated with the dysregulation of the human gene ATP1A3 for production of the protein ATPase Na+/K+ Transporting Subunit Alpha 3. This is the active enzyme component to catalyze the hydrolysis of ATP coupled with the exchange of sodium and potassium ions across the plasma membrane. Especially in neurons, this action creates the electric gradient across the plasma membrane by means of an electrochemical gradient of sodium and potassium ions. This catalytic ATPase enzyme is a protein that provides the energy for active transport of nutrients and is a P-type cation transporter in the subfamily of Na+/K+−ATPases. The ATP1A3 protein controls the gradients of Na and K ions across the plasma membrane needed for osmoregulation, and sodium coupled transport of organic and inorganic nutrient molecules that are responsible for the electrical excitability of nerve and muscle. This enzyme is composed of two subunits, a large catalytic subunit (alpha) and a smaller glycoprotein subunit (beta). The goal of enhancing autistic and perhaps even neurotypical mental cognition must be to assist this process even when the genetic production of ATP1A3 protein is dysfunctional. A reasonable objective to assist autistic persons is to create a substitute regulatory molecule that performs a similar catalytic task and can restore a more proper electric and electrochemical potential in neurons. Neural plasticity is controlled by epigenetic factors as well as genetic factors. The epigenetic signals of interest arise within the complexities of the cellular respiration cycle. No state of the art exists to assist neural cells to regulate the performance of this more subtle regulatory task.

What is therefore needed is a multiplexed solution for effectively extinguishing the mechanisms leading to reduced membrane potentials related to neurological disorders. Desirably, such a general treatment for autism spectrum disorders as well as aging related cognitive preservation should include a prophylactic enhancement of nootropic function able to overcome the electrochemical deficits of aging human neural cells. Therefore, to maintain or improve mental function and to restore autistic cognitive facilities, it is believed the present invention can provide such a solution using an artificial biological and electrochemical design to promote and improve the regulation of existing neurological functions.

SUMMARY

This invention is a small thiol-containing fullerene compound derivatized with both glutathione (GSH) and adenosine phosphates such as adenosine triphosphate (ATP) with enhanced utility to directly inactivate reactive oxygen species (ROS) and prevent ROS initiated reactions.

The invention provides embodiments of a composition having a fullerene having a cage structure and having at least one of a first functional group and at least one of a second functional group. The first functional group includes a glutathione that can accrue negative charge. The at least one second functional group includes at least one phosphate, in which phosphorous has an oxidation state of five, and in which biochemical reduction-oxidation (REDOX) reactivity is reversible. In further embodiments, the at least one second phosphate functional group includes an adduct of at least one adenosine phosphate functional group, in which phosphorous has an oxidation state of five. In selected embodiments, a mixture of these composition embodiments is provided, in which the first functional group includes a glutathione and the at least one second phosphate functional group includes an adduct of at least one adenosine phosphate functional group, in which phosphorous has an oxidation state of five. In some additional embodiments the fullerene includes C60 fullerene, and the first functional group includes a reduced or an oxidized glutathione. In yet still other embodiments, the fullerene includes a C60 fullerene or a redox metabolite thereof, and the first functional group includes a reduced or an oxidized glutathione, in which the redox metabolite adducts up to six electrons, and up to five protons in any combination.

The invention also provides a topical composition, having a fullerene with a cage structure with a hydrophobic region at unreacted carbon regions of the cage structure that is capable of reversibly storing as many as six protons, having at least one functional group including a glutathione that can accrue negative charge, and having at least one functional group including at least one phosphate, in which the phosphorous has an oxidation state of five, or including an adduct of at least one adenosine phosphate functional group, in which the phosphorous has an oxidation state of five, or including an effective mixture thereof. In some embodiments of the topical composition, the formula for the composition is C60(glutathionexphosphate)$_x$, where x includes between about one to about fifteen phosphate groups, having a typical value of 5 phosphate groups. Some other embodiments of the topical composition include a free-radical scavenging function and an associated anti-oxidant function when dissolved in water having from about 0% to about 30% by weight glycerol. Some further embodiments of the topical composition include an ultraviolet absorbing and sunlight protective function when used to provide REDOX reaction assisted cellular repairs.

The invention also provides a pharmaceutical composition having a C60 fullerene with a carbon cage structure, having at least one adenosine phosphate functional group in which phosphorous has an oxidation state of five, and additionally having at least one glutathione functional group. In some pharmaceutical composition embodiments, a molecular species has at least one negatively charged functional group and at least one neutral or positively charged functional group. In other pharmaceutical compositions, a formula for the composition is C60(glutathionexadenosine phosphate)$_x$, where x comprises between about one to about three adenosine phosphate groups. Still further pharmaceutical composition embodiments include physiological metabolites having an allosteric chemical bond to histone signaling effectors of DNA methylation. In some of these embodiments the formula for the composition includes C60(glutathione))(adenosine phosphate)$_x$ where x is between about one to about three phosphate groups and the composition further including a solvating mixture of about 70% glycerol and about 30% propylene glycol. Such compositions can be flash vaporized at about 260 degrees C. to create an inhalant aerosol.

These and other advantages of the present invention will be further understood and appreciated by those skilled in the art by reference to the following written specifications, claims and appended drawings.

Some embodiments are described in detail with reference to the related drawings. Additional embodiments, features, and/or advantages will become apparent from the ensuing description or may be learned by practicing the invention. In the FIGURES, which are not drawn to scale, like numerals refer to like features throughout the description. The following description is not to be taken in a limiting sense but is made merely for describing the general principles of the invention.

BRIEF DESCRIPTION OF DRAWINGS

FIG. 5 is an illustration of molecular structures of a glutathione reaction with C60 to form C60-GSH.

Figure 1:
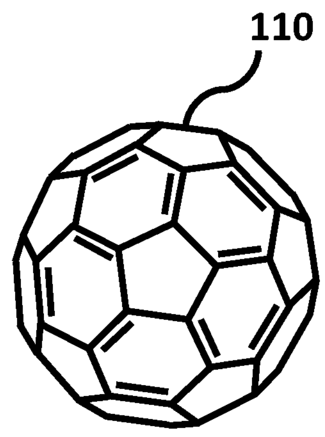
FIG. 1 is an illustration of molecular structures of the neurotransmitter glutathione, trisodium phosphate, and C60 fullerene.

Embodiments are described in detail with reference to the related drawings. Additional embodiments, features, and/or advantages will become apparent from the ensuing description or may be learned by practicing the invention. In the FIGURES, which are not drawn to scale, like numerals refer to like features throughout the description. The following description is not to be taken in a limiting sense but is made merely for describing the general principles of the invention.

DETAILED DESCRIPTION

The following detailed description, taken in conjunction with the accompanying drawings, is merely exemplary in nature and is not intended to limit the described embodiments or the application and uses of the described embodiments. Any implementation described herein as "exemplary" or "illustrative" is not necessarily to be construed as preferred or advantageous over other implementations.

Furthermore, there is no intention to be bound by any expressed or implied theory presented in the preceding technical field, background, brief summary or the following detailed description. It is also understood that the specific devices, systems, methods, and processes illustrated in the attached drawings, and described in the following specification, are simply exemplary embodiments of the inventive concepts defined in the appended claims that there may be variations to the drawings, steps, methods, or processes, depicted therein without departing from the spirit of the invention. All these variations are within the scope of the present invention. Hence, specific structural and functional details disclosed in relation to the exemplary embodiments described herein are not to be interpreted as limiting, but merely as a representative basis for teaching one skilled in the art to variously employ the present embodiments in virtually any appropriate form, and it will be apparent to those skilled in the art that the present invention may be practiced without these specific details.

Various terms used in the following detailed description are provided and included for giving a perspective understanding of the function, operation, and use of the present invention, and such terms are not intended to limit the embodiments, scope, claims, or use of the present invention.

Definitions

The use of acronyms for common biochemical molecules is well understood in the cellular respiration cycle, however to avoid confusion with potentially non-standard usage, effort is made to refer to these by definition in the present document, such that the following abbreviated terms for these substances will be used throughout:

CD38 is a multifunctional transmembrane glycoprotein found in humans that can operate as an enzyme, wherein it is responsible for the synthesis of at least two Ca2+ messenger molecules. It also operates as an antigen, wherein it is involved in some aspects of the innate immune inflammatory response, as well as in regulating cell adhesion, differentiation, and proliferation. CD38 is expressed on the surface of activated lymphocytes. The extracellular domain of CD38 is known to have bendable and positively charged extended N terminus residues.

Tumor Necrosis Factor alpha (TNF alpha), is generally understood to be an inflammatory cytokine produced by macrophages and monocytes during acute inflammation. It can be responsible for a diverse range of signaling events within cells, leading to programmed cell death or apoptosis.

NFkB, is used to represent nuclear transcription factor kappa B, considered to be a regulator of innate immunity. It regulates the expression of multiple inflammatory and immune genes and is known to be involved with chronic inflammatory diseases.

The present invention provides a multiplexed solution for effectively extinguishing the mechanisms leading to reduced membrane potentials related to neurological disorders. Desirably, such a general treatment for autism spectrum disorders as well as aging related cognitive preservation should include a prophylactic enhancement of nootropic function able to overcome the electrochemical deficits of aging human neural cells. Therefore, to maintain or improve mental function and to improve autistic cognitive facilities, it is believed the present invention can provide such a solution using an artificial biological and electrochemical design to promote and improve the regulation of existing neurological functions.

Embodiments provide a small thiol-containing fullerene compound derivatized with both glutathione (GSH) and adenosine phosphates such as adenosine triphosphate (ATP) with enhanced utility to directly inactivate reactive oxygen species (ROS) and prevent ROS initiated reactions. This composition tethers a fullerene, well known as a free radical scavenger, to glutathione, the most abundant non-protein thiol providing several vital functions such as direct scavenging of free radicals, detoxification of electrophilic compounds, modulation of cellular redox status and thiol-disulfide modification of proteins. Simultaneously, this composition tethers a fullerene (e.g., C60) to adenosine phosphates, where such phosphates are essential to the regulation of cell signaling and repair pathways, such as by phosphatizing the sirtuins. This novel composition directs mitochondria and modulates cellular homeostasis by self-adjusting the balance among cellular respiration, protein synthesis (anabolism), protein utilization, and recycling (catabolism). It also regulates innate immune responses resulting in the disturbances of cellular processes that may cause an oxidant or antioxidant imbalance, by coupling a reductant group to an oxidant group on the same structure, while preserving free radical and electron charges on an intermediary capacitive fullerene charge storage core molecule functioning as a free radical recombination and detoxification center. Antioxidants of indirect action influenced by this composition include biological phase II detoxifying enzymes, which contribute to biosynthesis, the recycling of thiols and NAD+, and the excretion of oxidized, reactive secondary metabolites. In general, phase II enzymes may include glutathione-S-transferase (GST) isozymes, NADP (H) counterions to quinone oxidoreductase (NQO1), gamma glutamate cysteine ligase (g-GCL), glutathione peroxidase (GPx), glutathione reductase (GR), and stress response proteins such as heme oxygenase (HO)-1 and the chains of ferritin. Other embodiments include a vapor method of delivery of compositions to regenerate neural cell function with age as well as to enhance cognitive function in autism spectrum disorders and other neurological deficits. This cellular redox function additionally serves as an excellent topical cell regenerator. In yet other embodiments, this same set of redox functions is used to confer protection to external skin cells, thereby conferring skin protection from sunlight damage and aging processes that lead to irregular skin pigmentation and cellular oxidative stress.

A nanoparticle composition is provided to improve cognitive well-being in both aging related neural decline, and in autism, to remediate reductive and oxidative stresses at mitochondrial lipid membranes by careful design consideration of a molecule having both cholesteric affinity and REDOX capability to confer protective functions to the normal operation of mitochondria and the cellular organelles to which they associate, especially those mitochondria in neural cells and brain tissue. The following fullerene composition is therefore designed to improve cognitive bioenergetics by increasing the electrical potential available for neural function. The composition of derivatized fullerenes is provided with at least one derivatized adenosine (mono-, di-, tri-) phosphate, and desirably also an equal proportion of derivatized glutathione.

One aspect of the present invention is to couple either a C60 fullerene adenosine phosphate glutathione with positive charged macrophages of the innate immune system having functional amine groups as part of their inflammatory antigens. Positively charged amines expressed on human protein CD38 at the surface of lymphocytes are part of the innate immune system that can carry the composition of the present invention via negatively charged portions of the fullerene adenosine phosphate functional groups. This aspect serves as one type of plasma delivery system for fullerene GSH-ATP and the derivatives fullerene GSH-ADP, fullerene GSH-AMP, or fullerene GSH-cyclic AMP.

In a related aspect, the cellular incorporation of fullerene GSH-ATP of the present invention directly results in an inhibition of the unfolded protein response (UPR) pathways of mitochondria. This aspect is enabled by the antioxidant and free-radical scavenging that is associated with fullerenes. One characteristic of this aspect is the separation of positive and negative charges on functional groups bonded to the core fullerene molecule. The GSH adduct obtains a positive charge, and the adenosine phosphates obtains a negative charge. This space separated charge allows enhanced free radical recombination in biological aqueous media such as the cytosol or water based cell fluids.

In a related aspect, the cellular incorporation of fullerene glutathione phosphates (C60-$PO_4$) functions substantially in similar manner to glutathione adenosine phosphates. In particular, the phosphate functional group can participate in both respiration and enzyme catalyzed reactions. The space separated charges of the fullerene glutathione phosphates allow enhanced free radical recombination in aqueous media such as in the cytosol, or inside of mitochondria.

In another aspect, fullerene adenosine phosphate glutathione is used to phosphorylate allosteric sites on sirtuins, a type III histone deacetylase. This makes the sirtuin more able to deacetylate histones onto which DNA is wrapped, causing the histones to present primary amines which can then obtain a proton from the nuclear cytosol to from positive charged amine groups.

In a related aspect, fullerene glutathione adenosine phosphates or fullerene glutathione phosphates may express both positive and negative charges at either of their functional groups. This design feature serves to create multiple charge-coupled adducts between the central negative charged phosphate ladder rungs of DNA and the amine positive charge on chromatin on which the DNA loops are bound to further stabilize the silencing of neurological deficit related DNA genes or gene groups from excessive transcriptional expression.

In another aspect, the novel coupling agents being functionally bound fullerenes serve to confer instant neuroprotection from ineffective catabolism and anabolism, while providing homeostasis of mitochondrial membrane polarization. Defects of lysosomal catabolism influence the function and structural characteristics of the MAMs both in autism and in aging associated neuropathy. The fullerene adenosine phosphate adducts of the present invention are therefore designed to expedite storage of electrons and protons. This expedites neural remodeling of both anabolic and catabolic deficits by the interposition between the mitochondrion and the endoplasmic reticulum (ER) as well as between the mitochondrion and other cellular organelles. This neuroprotective feature is of nutritional health maintenance as well as of pharmaceutical interest to help alleviate deficits associated with autism, amyotrophic lateral sclerosis (ALS), and other cognitive dysfunctions.

One aspect of the fullerene adduct embodiments described herein is their ability to reside at the membrane-proximal region consistent with the abilities of fullerenes to interact with the hydrophobic tails of lipid rafts, while their hydrophilic adducts associate better to the hydrophilic head of these same lipid rafts, thereby keeping them in proximity to a mitochondrion cell membrane or endoplasmic reticulum.

In a related aspect, the fullerenes of the present invention express negative charges at the phosphate functional groups to confer the ability to form an adduct with positively charged long side chains of the inflammatory antigen and human proteins such as the human innate immune defense cytokines, and exemplary CD38. This has the immediate effect of temporarily denaturing the positively charged extended N terminus residues of cytokines and CD38, when in proximity to a mitochondrion cell membrane or endoplasmic reticula.

In another aspect, the GSH-ATP fullerenes provide protection to NAD+, which is consumed by autoimmune dysregulation. For example, the epigenetic programming of an immune response may be excessive and unable to restore to normal levels. In particular, the innate immunity conferred by CD38 consumes NAD+. The electrical nature of the composition allows stabilization of the concentration of NAD+ in cellular respiration for reduction-oxidation pathways that require significant amounts of NAD+. This aspect leads to improved function of mitochondria of neurons in the brain, and therefore provides significantly improved electrical energy output from neural cells.

In another aspect, fullerenes are generally known to reduce the inflammatory cytokines such as TNF-alpha and NFkB because they scavenge and terminate the free radicals that are associated with inflammation. The negatively charged adenosine phosphate adduct to the fullerene in disclosed embodiments is superior in its ability to attract to and countercharge the positively charged amine groups associated with cytokines and other inflammatory molecules having positive charges. Likewise, CD38 expression in several cell types is induced by the presence of the inflammatory cytokines. Therefore, the fullerene GSH-ATP of the present invention, together with its metabolites, reduce or eliminate the conditions that give rise to CD38 expression.

One aspect of the fullerene GSH-ATP fullerenes is their placement into the gaps between the mitochondrion associated membranes, or MAM. This function is to enable increased catabolism between MAM, for example the catabolism between the Golgi complex and the mitochondrion, or between the endoplasmic reticulum and the mitochondrion. What is catabolized, or broken down, are the variety of sugars and proteins required as components to build or to rebuild new cell components. Non-limiting examples of cellular catabolized molecules include glycolsphingolipidoses, sphingolipids, and carbohydrates.

In a related aspect, the placement of fullerene GSH-ATP into MAM increases the efficiency of catabolism by storing electrons and protons. The catabolic restructuring of topical eye cells at the cornea using the composition of this invention is one example of using the energy of sunlight to power the REDOX reaction of mitochondria in the regeneration of clear and transparent tissues at oxidized cataracts without recourse to surgical excision of clouded proteins or the use of foreign tissue transplants to rescue vision from clouded eye tissues.

In another related aspect, the placement of fullerene GSH-ATP into MAM removes accumulated proteins and detritus that have blocked the ability of the mitochondrion to function with proper electrical potential or bioenergetics, thereby restoring the catabolic function that normally declines with age and restoring health over senescence.

In a functional aspect, the presence of fullerene GSH-ATP orients in the electric field at the MAM with the positive face of glutathione toward the negative potential, and the negative face of the phosphate ion directed at the positive potential. Outside of a strong electric field such as found at the MAM, the binding of cellular hydrogen in physisorption to fullerene derivatives is without dissociating or splitting, and the binding strength is weak and highly localized, limiting hydrogen storage efficiency and electron charging capacity on the fullerene core molecule. To overcome these problems, the composition of the present invention utilizes a different method. On interposition within the MAM, this proximal abutment generates a high electric field near the surface of the fullerenes to polarize and attract hydrogen molecules or ions with enhanced binding strength that is delocalized with respect to the core fullerene molecule. This aspect is promoted by the spatial orientation of the localized negative charge on the adenosine phosphate and the positive charge on the glutathione functional group in an electric field, and results in enhanced electron exchange capacity on the inner fullerene core molecule that is resistively coupled to these two separated charges. The reversible hydrogen storage effect allows the core fullerene molecule to store atomic hydrogen as protons as well as to charge and discharge electrons while maintaining orientation with respect to opposing charges in the separate spatial regions of this molecular structure for the purpose of enhancing the process of cellular respiration and electron charge transfer in close proximity to mitochondria or the plasma membrane of a cell.

Advantageously, at least some of the poly-phosphorylated fullerene molecules express geometric localization of polyphosphates to one cluster at one face or hemisphere of the substantially spherical carbon molecular cage of the fullerene structure, to enable a hydrophilic face directed at mitigating reactive oxygen species at the interface between the endoplasmic reticulum (ER) of the mitochondrial cell membrane and the cytosol or water based fluids abutting the ER, while allowing a hydrophobic region of the fullerene carbon face to reversibly attract to an associated proximal cell lipid membrane, or a microtubule, or an actin filament. The ability of the fullerene to terminate free radicals in these regions avoids damage of cell structures by ROS that can leave cells susceptible to invasive pathogens.

In the drawings wherein like elements are represented by like numerals throughout:

FIG. 1 illustrates the molecular structures of some components and raw materials. Buckminsterfullerene is a spherical chemical cage representing 60 aromatic carbon atoms with formula C60, also known herein as a fullerene molecule 110. The chemical structure representing the sodium salt form of the inorganic triphosphate molecule 130 has three negatively charged oxygen atoms to countercharge each sodium ion, as shown for one such group at the bracket region 140. The oxidation state of the phosphorus atom in the phosphate is +5. It is understood that inorganic phosphate reversibly replaces some positively charged sodium ions with positively charged hydrogen protons when sodium phosphates are dissolved in water. Reduced glutathione 150 is a natural antioxidant as well as a neurotransmitter that is obtained through the diet as well as being produced endogenously in the body and brain of humans and animals. Substances 110, 120, 130, and 150 may be used to create the nanoparticle compositions according to these teachings.

Figure 2:
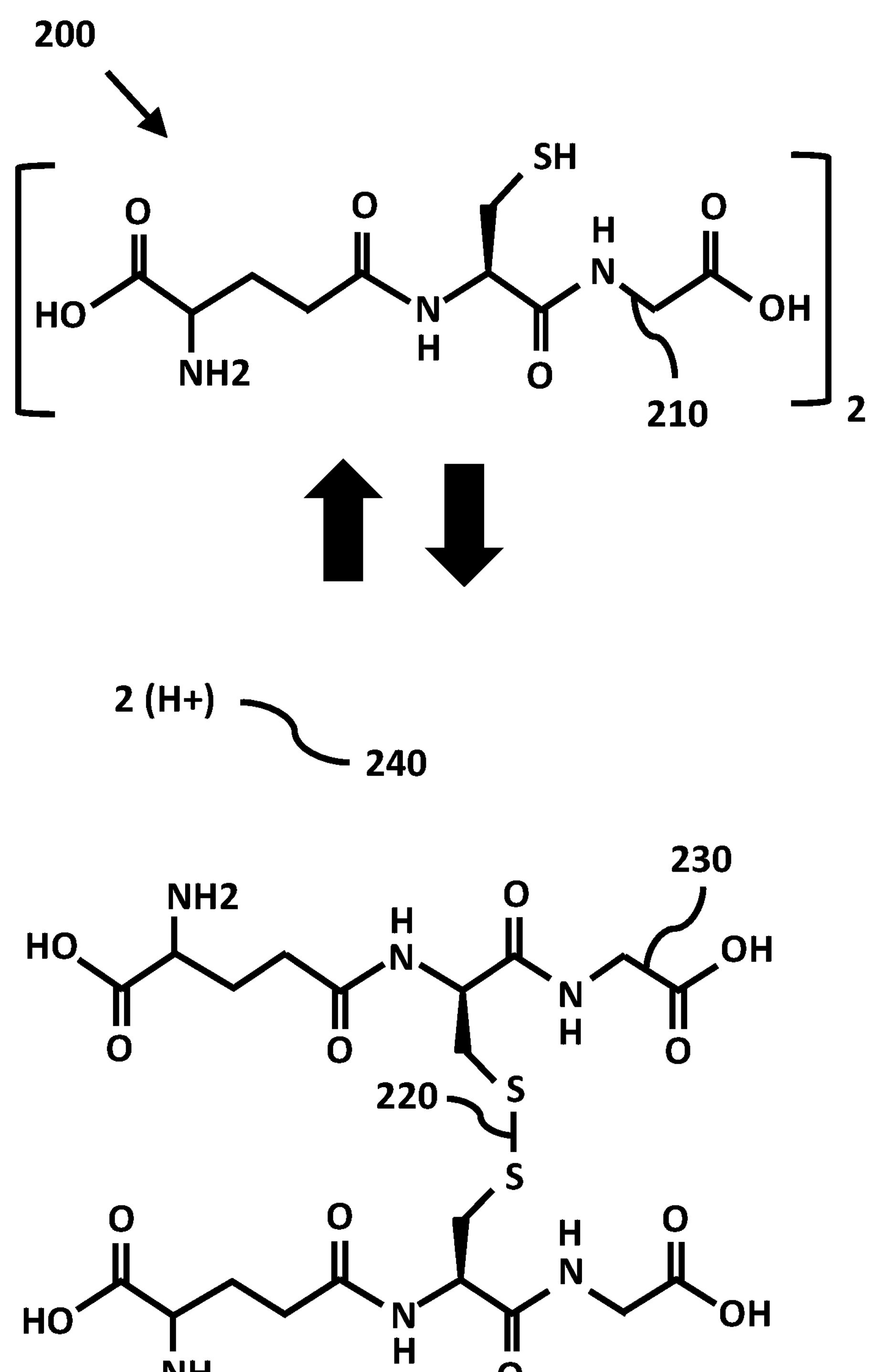
FIG. 2 is an illustration of molecular structures of the reversible oxidation of the neurotransmitter glutathione (GSH) into dimeric glutathione (GSSH).

FIG. 2 illustrates the molecular structures 200 of the reversible biochemical oxidation reaction of glutathione 210. Two of the reduced form of glutathione molecules 210 become oxidized into a dimeric form of glutathione having a characteristic sulfur to sulfur bond 220. In the biochemical process of cellular respiration, the oxidized form of glutathione 230 (also known by the abbreviation GSSH), is reduced by two hydrogen protons 240 reversibly into two discrete glutathione molecules (also known by the abbreviation GSH). This reversible biological oxidation and reduction (redox) process between GSH and GSSH will likewise take place in the context of the various derivatives of glutathione specified as a functional operation of the GSH functional group at the nanoparticle composition of these teachings.

Figure 3:
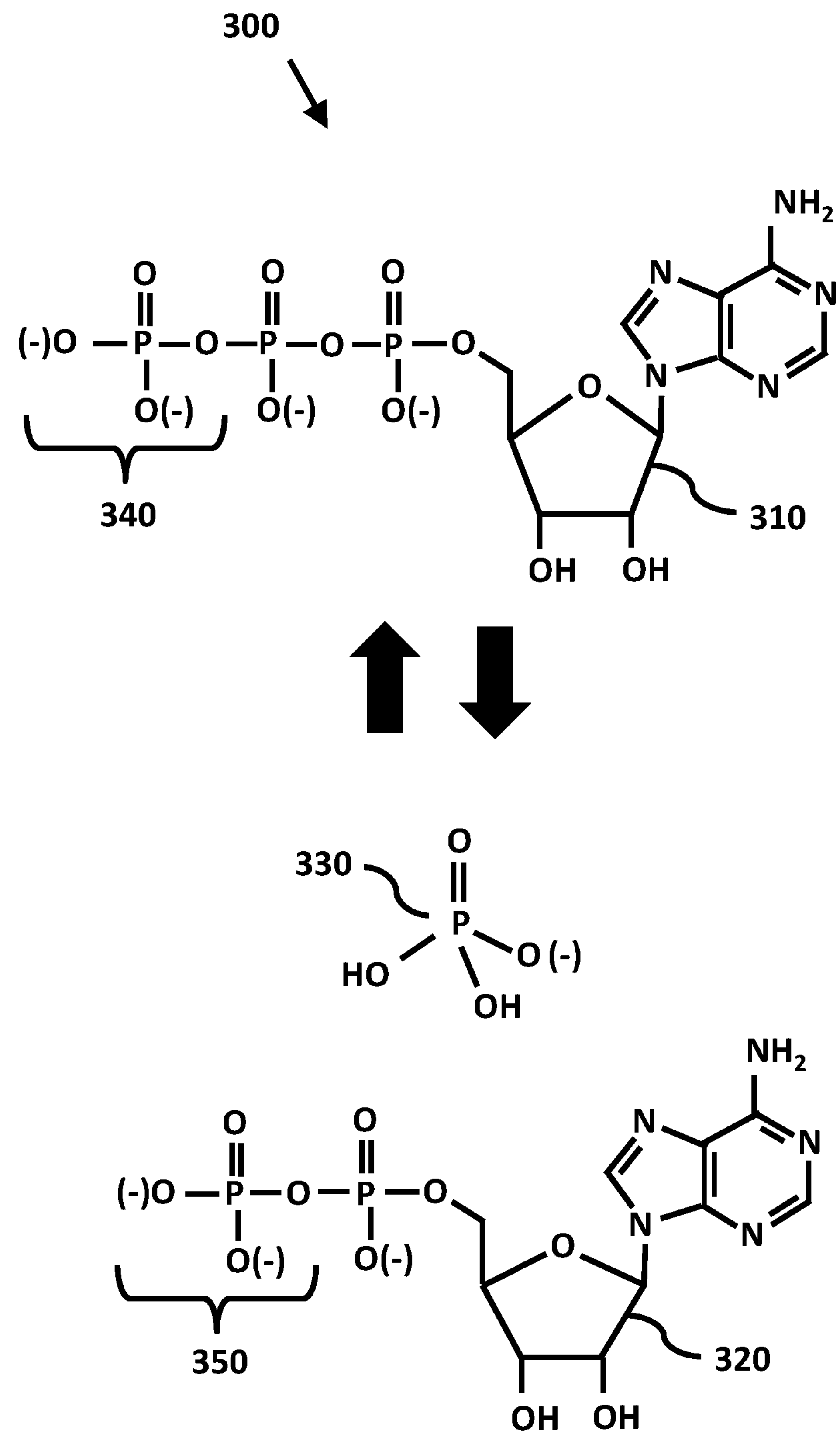
FIG. 3 is an illustration of molecular structures of the reversible mineral phosphate reactions of the neurotransmitter adenosine triphosphate (ATP).

FIG. 3 illustrates the molecular structures 300 of the reversible biochemical phosphate reactions of the neurotransmitter adenosine tri-phosphate 310. The adenosine triphosphate 310 reversibly disassociates into adenosine diphosphate (ADP) 320, with the loss of one free inorganic mineral phosphate group 330, where this reaction is shown by the downward direction of the heavy black arrow. ADP and a mineral phosphate can again become bonded, where this reaction is illustrated by the upward direction of the heavy black arrow, to form the phosphate group 340 on ATP 310. This chemical process is part of the chemical respiration of the cell at physiological pH. It is understood that ADP 320 may also lose one more phosphate group 350 to generate adenosine monophosphate (AMP) in a similarly reversible manner. The AMP and the related cyclic adenosine monophosphate (cAMP) structures are sufficiently well understood as reversible metabolites of ADP and ATP and will react in like manner when used as a functional group of a nanoparticle according to these teachings.

Figure 4:
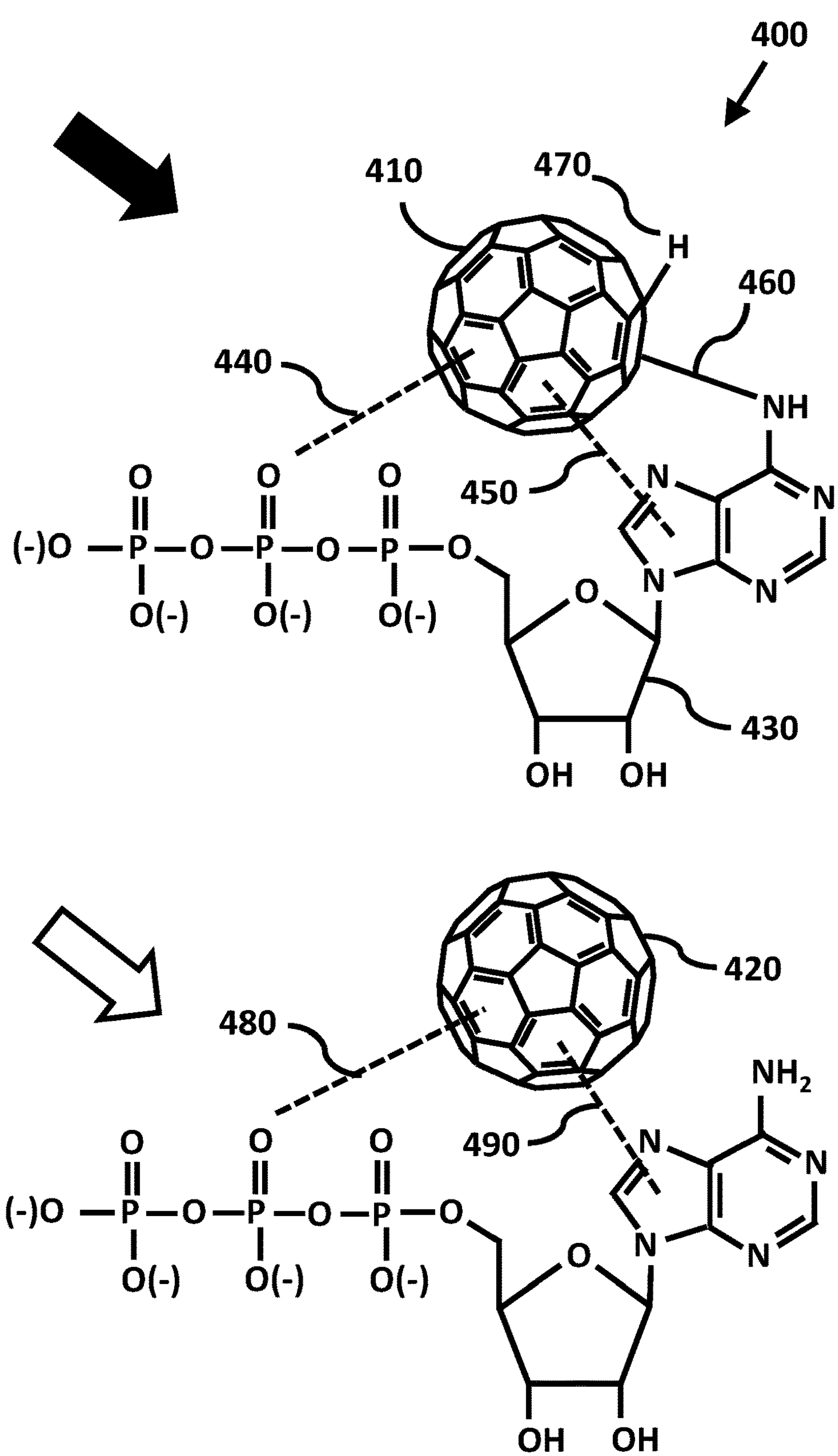
FIG. 4 is an illustration of the reaction of ATP with buckminsterfullerene (C60) to form C60-ATP.

FIG. 4 illustrates an exemplary fullerene adenosine triphosphate synthesis 400. The reaction of the neurotransmitter adenosine triphosphate 430 is with C60 fullerenes 410, 420. The amine functional group of adenosine triphosphate 430 may form two aromatic pi-pi stacking bonds 440, 450 and a covalent bond 460 at the amine nitrogen, with a transient hydrogen adduct 470 at neutral pH to form fullerene C60-ATP, where the product of this synthesis reaction shown by the direction of the large black arrow is favored above 55° C. However, adenosine triphosphate, may also form fullerene C60-ATP where the product of this synthesis reaction is shown by the direction of the large white arrow, forming two aromatic pi-pi stacking bonds 480, 490 which is more favored without an amine reaction below about 55° C. It is understood that metabolites of the fullerene adenosine phosphate nanoparticles will be reversibly oxidized and reduced by the gain or loss of phosphate groups in the manner illustrated for adenosine triphosphate in FIG. 3 in the context of this and the related adenosine phosphate fullerene compositions herein.

Figure 5:
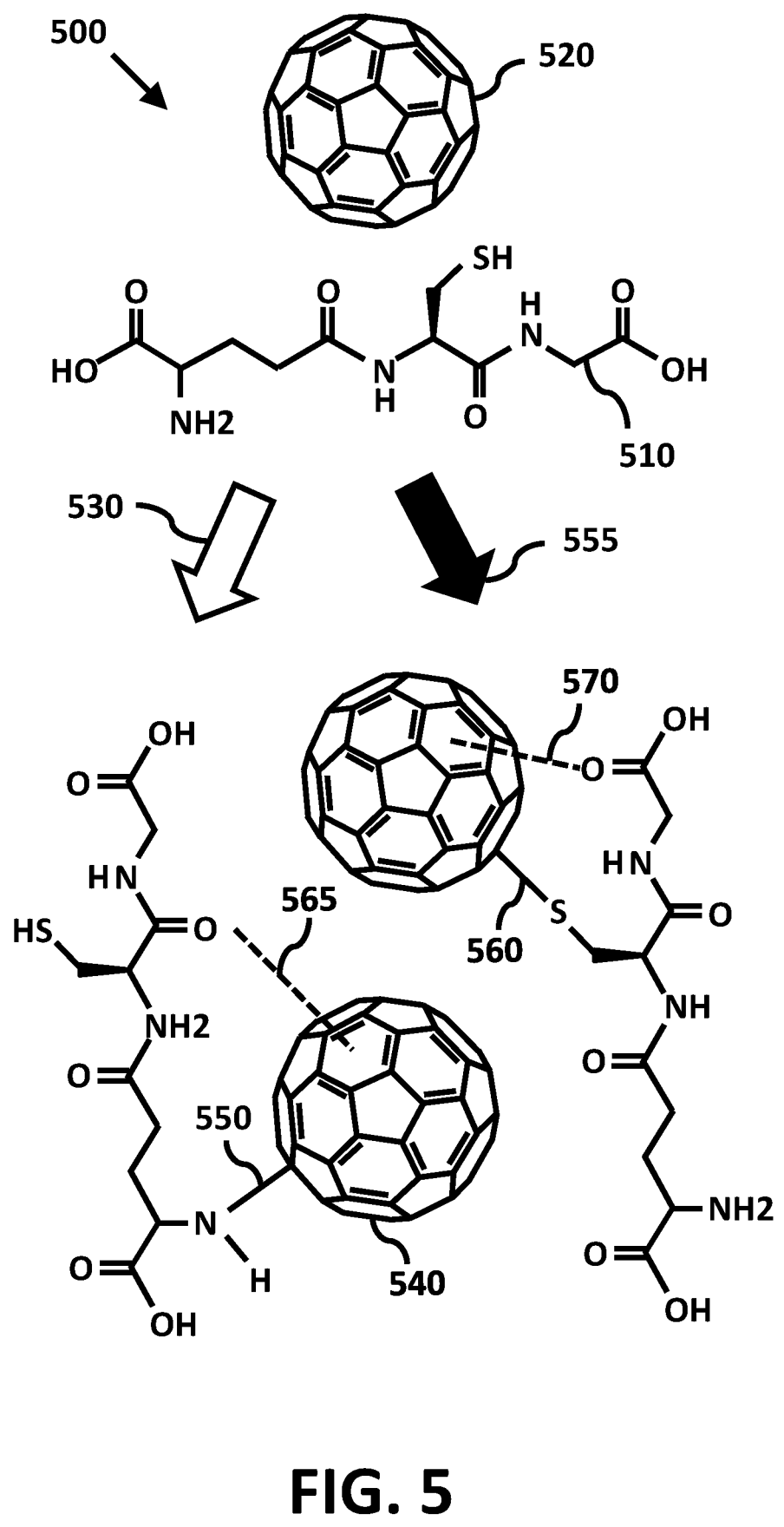

FIG. 5 illustrates molecular structures 500 for fullerene glutathione synthesis. The reaction of glutathione 510 with a C60 fullerene may proceed along the reaction pathway above 55° C. indicated by the direction of the large white arrow 530 at neutral pH to form C60-GSH 540 through a primary amine covalent bond 550. However, the reaction may proceed substantially along the reaction pathway below 55° C. indicated by the direction of the large black arrow 555 to form C60-GSH-ATP provided with a covalent sulfur bridge 560. In either reaction pathway, at least one pi-carbonyl bond forms as indicated by exemplary dashed lines 565, 570 which serve to stabilize the nanoparticle structures with fullerene. In each case it is understood that metabolites of the fullerene glutathione adenosine phosphates will be reversibly created in the manner illustrated for oxidized glutathione (GSSH) in FIG. 2, and in the manner of migrating phosphate groups illustrated in FIG. 3.

Figure 6:
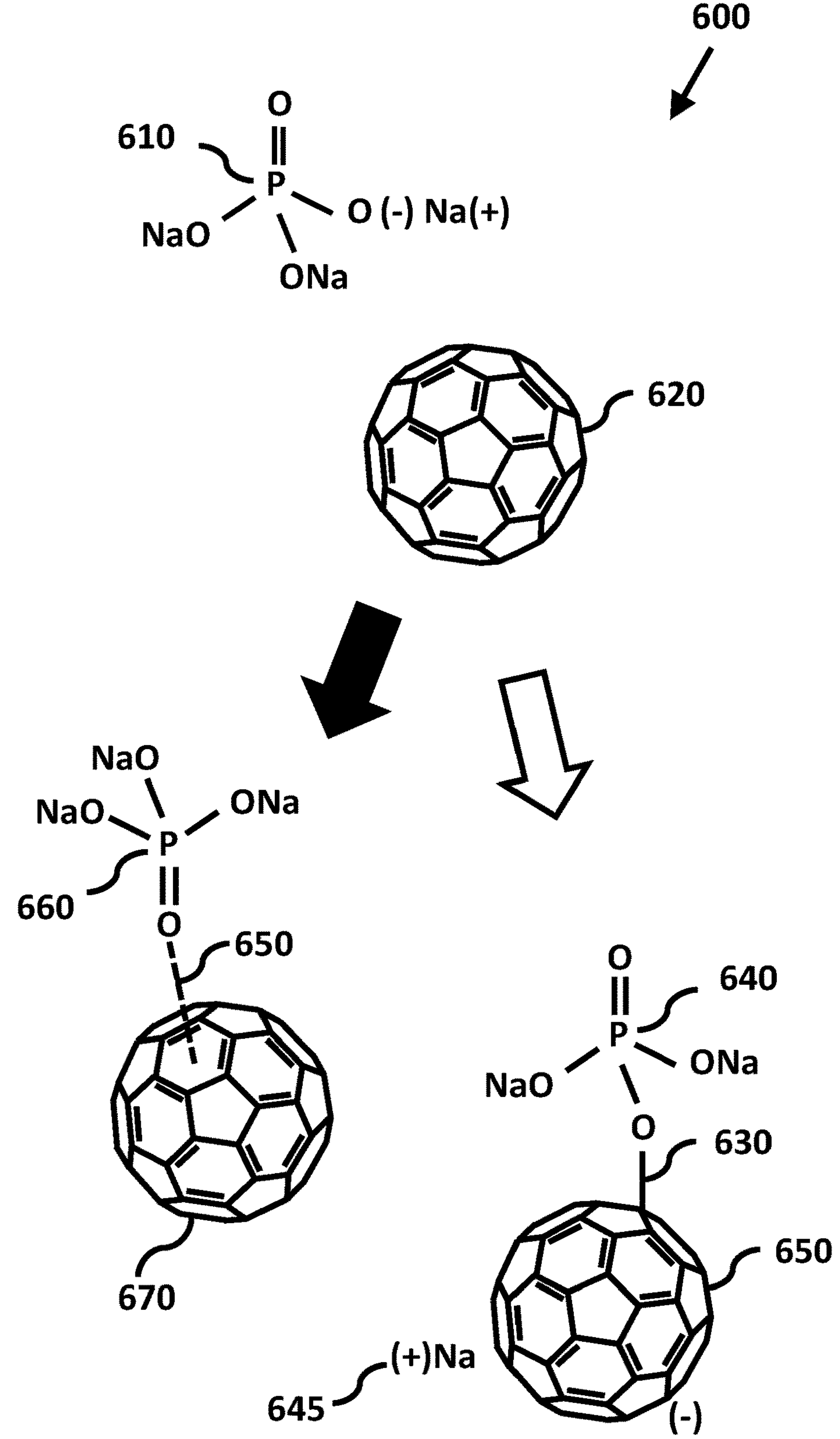
FIG. 6 is an illustration of the molecular structures of one inorganic phosphate reaction with C60.

FIG. 6 illustrates a C60 fullerene phosphate synthesis 600. The inorganic trisodium phosphate 610 from ATP or ADP is provided with three negative charged oxygen atoms that have counter-charged cations such as sodium which can become attracted to react with a C60 fullerene molecule 620. It is understood that multiple mineral sodium phosphate groups may react with C60 fullerene to create fullerene phosphates, where the reaction may proceed in the direction of the white arrow to form a transient oxygen covalent bond 630 between C60 650 and sodium phosphate 640, along with a sodium ion 645 that can become pi-cation associated with C60, 650. However, the reaction may also proceed in the direction of the black arrow to form a phosphonyl-pi bond as indicated by the dashed line 650 to stabilize the structure between the double bonded oxygen of phosphate 660 and C60 670. Shuttling of inorganic phosphates is widely utilized in the human body in ATP, ADP, and AMP. A substantial origin of the inorganic phosphate groups is from the adenosine phosphates, ATP, and ADP. Such phosphates assist with charge transport and shuttling in the electron transfer chain and the proton (H+) accumulation process using ATP synthase (ATPase) of cellular respiration at mitochondria. Medical evidence clearly points to a deficit in this type of shuttling for a wide range of autism spectrum disorders. Fullerene can help to anchor ionic species by van-der-Waals attraction to biological cellular structures between organelles inside cells, as well as to the organic peptides within cellular organelles such as the mitochondria where respiration takes place. The presence of both inorganic and organic functionality improves the cellular respiration process and overcomes some compatibility issues with malformed peptides and neuropeptides to help with energy production in the mitochondria of the brain for pathologies such as autism where ion shuttling, and electron transport are responsible for the pathology of autistic neurological deficits.

Figure 7:
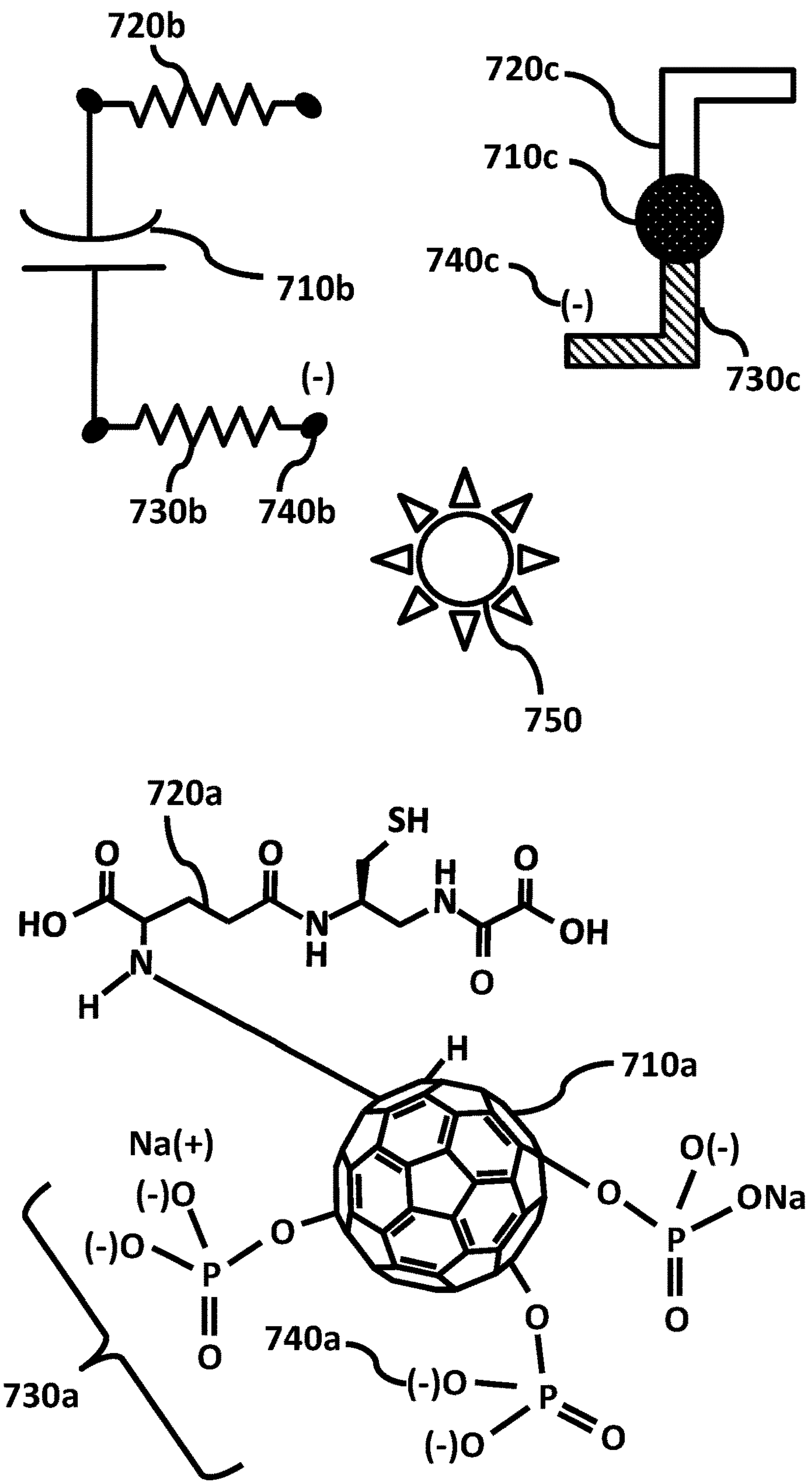
FIG. 7 is an illustration of the molecular structure of fullerene glutathione phosphates, and alternative electrical and iconic schematics representing the same.

FIG. 7 illustrates a dual neurotransmitter nanoparticle ensemble C60 fullerene phosphate glutathione using different schematic formats. The molecular structures for C60 710*a*, and GSH 720*a*, and phosphate 730*a* are also represented by circuit diagram illustrations with capacitor 710*b* corresponding to C60 710*a*, resistor 720*b* corresponding to GSH 720*a*, and resistor 730*b* corresponding to phosphate 730*a*, and likewise corresponding to iconic symbols 710*c*, 720*c*, 730*c*. Negative charges (−) arising from phosphates are represented by 740*a*, 740*b*, 740*c*. In the molecular structure representation, the core C60 fullerene 710*a* is covalently bonded to a pendant functional group of glutathione 720*a* and three pendant functional groups of phosphate 730*a*. The phosphate groups 730*a* may obtain multiple negative charges on oxygen at the loss of hydrogen or sodium cations during ordinary cellular respiration and cellular pH changes that take place during cellular respiration, anabolism, and catabolism processes. The origin of any phosphate can be the spallation from ATP, or ADP. The steric hindrance and insulative resistances of the functional groups on the fullerene 710*a* help to screen and stabilize any type of acquired charges, thereby providing the ability of the nanoparticle ensemble to be stable in both anionic (exemplary phosphate, chloride) or cationic (exemplary potassium, sodium or hydrogen) physiological environments. The storage of ionic charges at the nanoparticle ensemble is simultaneous with promoting ionic shuttling under a wide pH range.

Solar irradiation containing ultraviolet light 750, and reactive oxygen species created during respiration, will act to create free radicals in human tissues. Both fullerenes and glutathione function as free radical scavengers and antioxidants. The presence of phosphate groups 730*a* serve to anchor the nanoparticle composition into the phospholipids of the outside membrane of cells, or the internal membranes of cell organelles. This molecular composition also confers free radical protection from reactive oxygen species when it diffuses into the interior or inside regions of any cell. However, the presence of phosphate adducts helps to extend the chemical functionality of free radical scavenging into the citric acid portion of the cellular respiration cycle.

Figure 8:
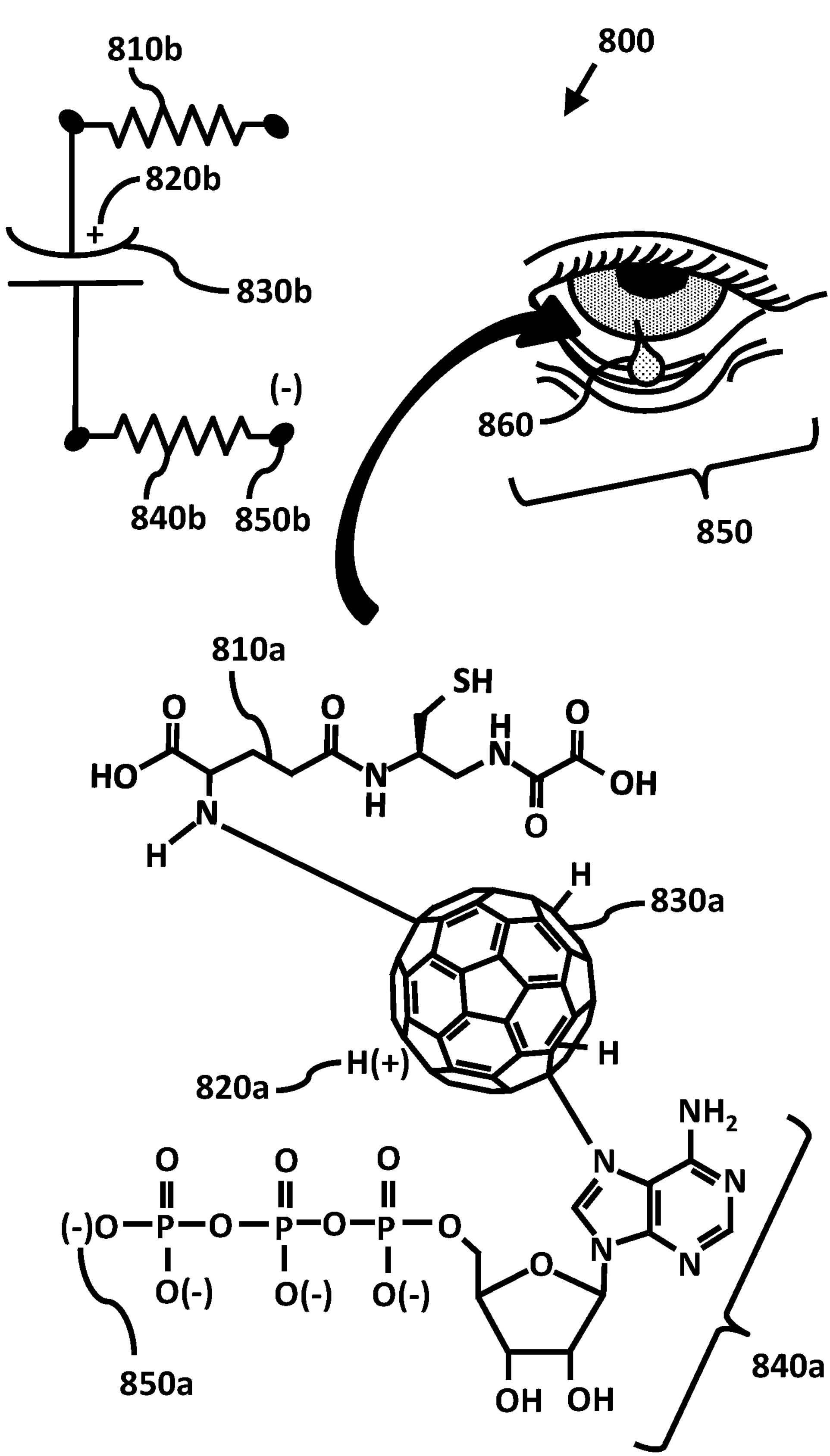
FIG. 8 is an illustration of the molecular structure of C60 fullerene glutathione adenosine diphosphate, electrical characteristics, and some embodied methods of use.

FIG. 8 illustrates a C60-GSH-ATP nanoparticle ensemble and a method of ocular application 800. The functional group of glutathione 810*a* and at least one positive charged hydrogen proton 820*a* are adducted to C60 830*a*. The functional group adenosine triphosphate 840*a* is provided with at least one negative charge 850*a* and may accrue a multiplicity of negative charges on the loss of protons at physiological pH. Phosphate group negative charges are sufficiently removed from the C60 830*a* that these do not influence the ability to store at least one positively charged proton 820*a*. This is represented in electrical schematic form by a positive charge 820*b* on capacitor 830*b* symbolizing the C60 830*a*. The circuit elements herein provide a way to understand some of the electrical functions that correspond to the molecular elements described for fullerene-ATP-glutathione derivatives. The ionic charge storage feature is provided by the dual neurotransmitter nanoparticle ensemble. This enables free-radical scavenging simultaneous with charge transfer for anions and cations to compensate for the deficit of these functions in a wide spectrum of autism spectrum pathologies. The molecular structures represented as a circuit schematic diagram clarify the role of the neurotransmitters ATP 840*b* and GSH 810*b* as molecular resistances able to transport localized charges. The ATP functional group collects stable negative charges shown at 850*b*. The C60 830*a* is represented by capacitor 830*b* and positive charges 820*b* are shown on one side thereof, while the C60 830*a*. It is to be understood that the fullerene C60 is equally well able to store both anionic (negative) and cationic (positive) ions.

As noted previously, in the presence of sunlight, reactive oxygen species and free radicals are formed in tissue. The C60-GSH-ATP composition may be dissolved into a liquid solution and applied into the eye 850 as represented by water drop 860, where the large curved black arrow indicates the nanoparticle dual neurotransmitter molecular structure is administered within the water drop to be introduced into the human eye 850 as an eyedrop 860 having pharmaceutical anti-cataract properties. The presence of multiple hydrogen protons remediates the aged and protein crosslinked corneal tissues, especially at night or during dark periods, to help restore cataract transparency by the REDOX reaction. Mitochondria within the ocular tissues can also enable REDOX voltages operating by means of the charge transfer process of cellular respiration, which then act as an electrically powered means to chemically reduce and repair the polymeric chains of oxidized corneal tissues as assisted by the electrical properties of the fullerene-GSH-ATP nanoparticle ensemble.

Fullerene-GSH-ATP is immediately suitable for administration as an ASD therapy agent to the lungs by means of aspirated delivery, and including the gastrointestinal tract, by means of ingested oral solutions, and including the eye or ocular tissues by means of eye drops 860.

Figure 9:
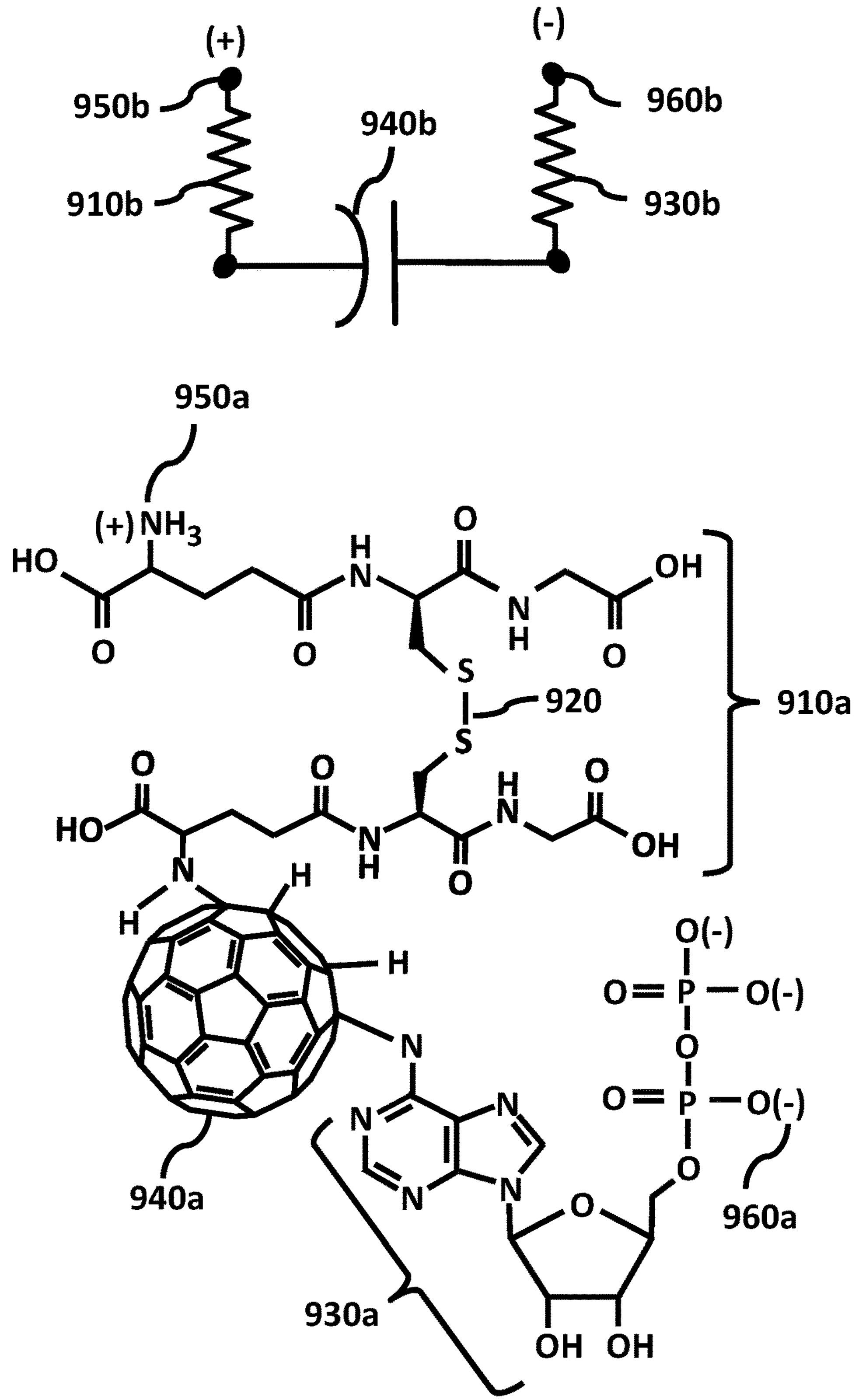
FIG. 9 is an illustration of the molecular structure of a C60 fullerene dimeric glutathione adenosine diphosphate metabolite, and an electrical schematic representing it.

FIG. 9 illustrates a C60 fullerene dimerized glutathione adenosine diphosphate. The pendant functional group of dimerized glutathione (GSSH) 910*a* is comprised of two glutathione molecules that have been oxidized to each other by the bridging sulfur to sulfur bond 920 and represents one of many possible metabolites of the present invention. The functional group of adenosine diphosphate (ADP) 930*a* is pendant from the core carbon cage molecule of C60 940*a*. It is to be understood that the dual neurotransmitter fullerene-GSSH-ATP is a metabolite where a phosphate group has been lost from ATP to form ADP, and where the glutathione has become oxidized, and that such metabolites are part of the acceptable biochemical variations that are reversibly produced in the human body as part of the REDOX function of this nanoparticle ensemble. Such reversible nanoparticle conversions maintain substantially equal function to perform their role as ionic shuttles, according to these teachings.

A positive charge on the GSSH can arise from the acquisition of a hydrogen proton onto the primary amine functional group 950*a*, which is represented in the electrical schematic of this dual neurotransmitter metabolite as 950*b*. Likewise, a multiplicity of negative charges can arise at the adenosine phosphate groups 960*a*, illustrated electrically as 960*b*. Both adenosine diphosphate group and oxidized glutathione do not influence charges that may be stored on the core fullerene. Charge storage by the fullerene 940*a* is represented by the schematic symbol of capacitor 940*b*. Positive charge on GSSH 950*a* is represented by charge 950*b*, where the glutathione functional group 910*a* is represented by electrical resistor 910*b*. The adenosine diphosphate functional group 930*a* is represented by electrical resistor 930*b*.

Figure 10:
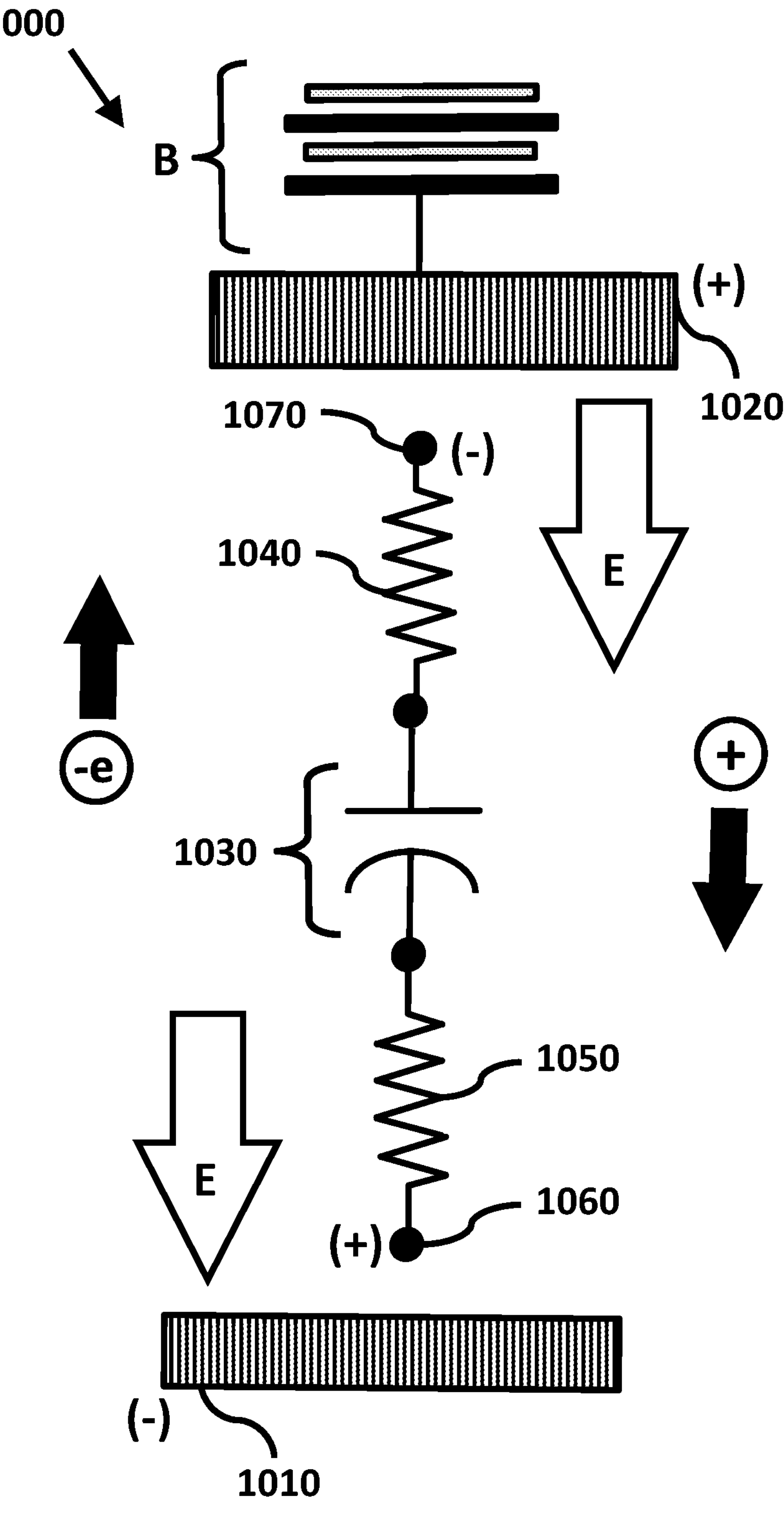
FIG. 10 is an illustration of the electrical schematic of a fullerene glutathione adenosine triphosphate dual neurotransmitter as it is oriented by the cellular electric field.

FIG. 10 illustrates an electric schematic diagram 1000 used to clarify the equivalent molecular device physics of the molecular composition of the present invention when utilized in an electric field between cell organelles. Organelle membrane 1010 is supplied with a net negative charge, and organelle membrane 1020 is supplied by a net positive charge. These differences in potential are generally understood to function as control signals for internal cell processes. The dual neurotransmitter C60-GSH-ATP operates to modify cell signal voltage as follows. The positive charge on membrane 1020 may arise from a histone acetyltransferase as found in a cell nucleus in chromatin, or by means of some redox reaction associated with a mitochondrion represented by the symbol for battery B. The negative charge on membrane 1010 may arise from the phosphate bridges associated with proximal deoxyribonucleic acid loops in the cell nucleus, or the release of a source of electrons which can arise because of some redox reaction associated with a biological process being contained by membrane 1010 such as by a cell membrane. Capacitance 1030 represents the charge storage ability of the core fullerene molecule. Resistance 1040 represents the adenosine phosphate, and resistance 1050 represents the glutathione molecule. Positive charge 1060 can be expressed on the glutathione molecule by the acquisition of a proton to an amine functional group. Negative charges 1070 can be expressed on any of the single bonded oxygen atoms of phosphate groups in the adenosine phosphate. The case of non-zero charges on either 1060 or 1070 can be necessary and sufficient to orient the glutathione fullerene adenosine phosphate molecule represented collectively by resistor 1040, capacitor 1030, and resistor 1050 with respect to the opposing charges on proximal abutting membranes 1010, 1020. The electric field represented by "E" is a vector pointing in the direction indicated by the two large white arrows and represents the origin at positively charged membrane 1020 and a destination at negatively charged membrane 1010. This field exists within a water-based medium called the cell cytosol which is provided with free moving electrons represented by encircled (-e), as well as free moving hydrogen protons represented by encircled (+), where the small black arrows adjacent to each indicates their respective direction of motion. Fullerene core molecule 1030 may capacitively store as many as about six electrons (or anions) and may form adducts with as many as about five protons (or other positive charged atoms), thus serving as a charging circuit element (a capacitor) for the shuttling of anions and cations. If for some biological process of catabolism, any adduct of the fullerene nanoparticle ensemble becomes removed, the fullerene can still act as a capacitance to store positive or negative charges as electrons, protons, cations, or anions. The presence of at least one charged adduct assures a preferred orientation of the nanoparticle ensemble with respect to the electric field.

Figure 11:
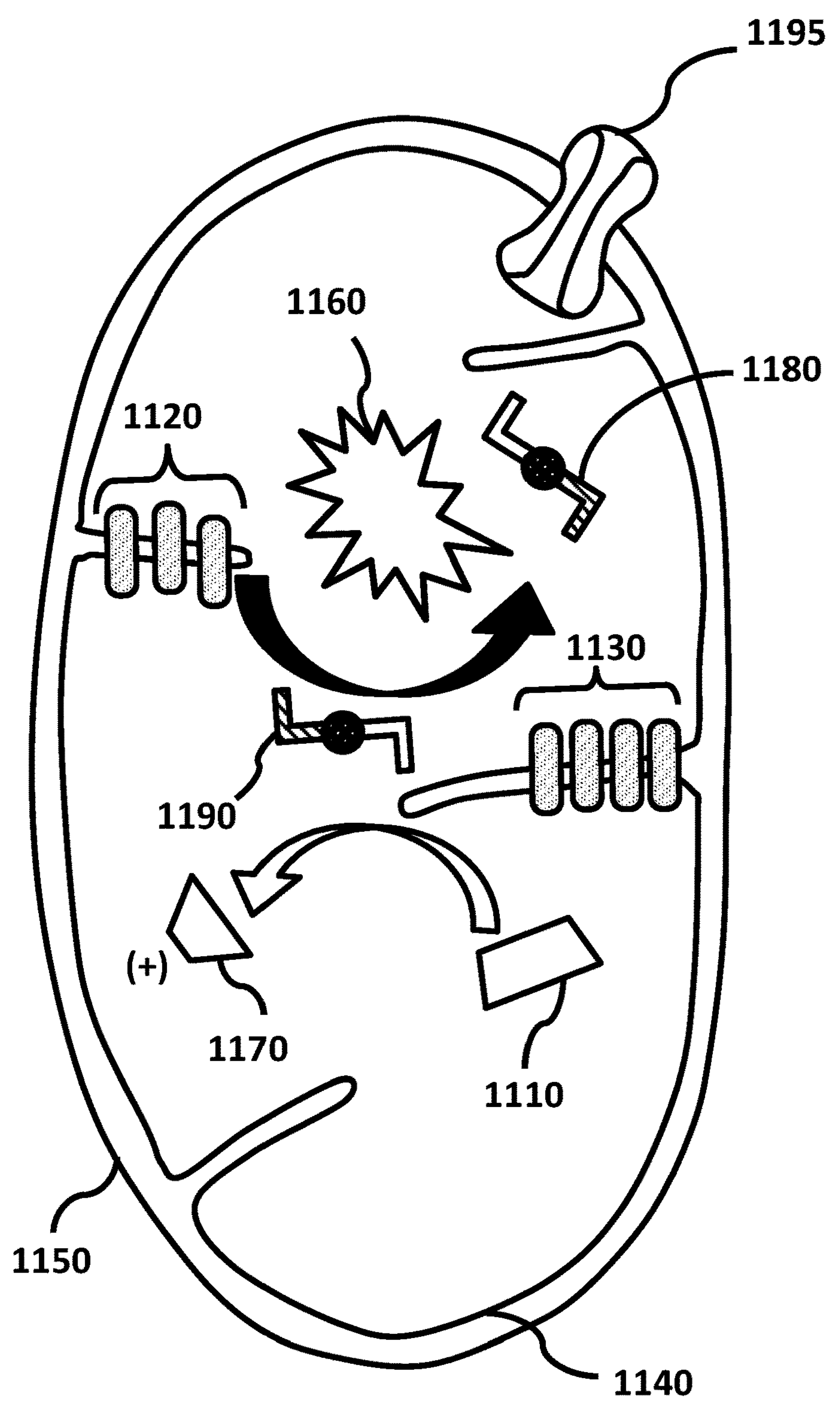
FIG. 11 is an illustration of charge coupled REDOX reaction enabled inside a mitochondrion by fullerene-GSH-ATP dual neurotransmitter.

FIG. 11 provides a schematic illustration of charge coupled REDOX enabled in a mitochondrion by fullerene glutathione adenosine phosphate nanoparticles 1180, 1190. Mitochondrial oxidative phosphorylation includes the process of electron transfer through the mitochondrial respiratory chain, trans-inner mitochondrial membrane ATPase proton pump, and generates the mitochondrial membrane potential, arriving at the final ATP generation. The mitochondria produce energy in the form of ATP by oxidizing carbohydrates, and by the release of hydrogen from fatty acids. Electrons derived from a molecule of NADH 1110 are passed sequentially through the electron transfer chain (ETC) complexes 1120, 1130. The energy released is used to pump protons into the mitochondria intermembrane space 1140 from outside of the region bounded by the endoplasmic reticulum membrane 1150 to create a mitochondrial membrane potential, or voltage, which is coupled to ATP synthesis. As protons flow across the mitochondrial inner membrane back into the mitochondrial matrix, inorganic phosphorus is bound to ADP to produce ATP in a reversible chemical reaction as illustrated in FIG. 3. Some of the electrons leaked from the ETC complexes 1120, 1130 move in the direction of the curved large black arrow to donate to molecular oxygen (02) or to produce superoxide anion ($O_2$—), hydrogen peroxide ($H_2O_2$), and other reactive oxygen species indicated by the spiked schematic symbol 1160. The autistic brain has a surplus of GABA inhibitory neurons, which lead to over-polarization of mitochondria in these neurons, and an excess of ROS that is released into the mitochondria and then the brain. The presence of ROS results in a decrease of NADPH and nicotinamide adenine dinucleotide or NAD(+) 1170 that is formed from it as indicated by the direction of the large curved white arrow. However, ROS can be quenched by proximal fullerene glutathione adenosine phosphates 1180, 1190 by attracting and recombining multiple ROS free radicals. This free radical quenching process takes place conventionally in well-known ambient cellular respiration reactions, but it is especially and highly catalyzed by the charge attraction of the central fullerene core molecule of each fullerene glutathione adenosine phosphate nanoparticle 1180, 1190, while simultaneously and unconventionally providing a novel delocalized site on to which to proximally store as many as six negative electron charges that were leaked from the ETC complexes. Porins 1195 are the most abundant proteins in the mitochondrial outer membrane. The porins operate to promote the exchange of ions and small molecules, including NADH, and ATP across the mitochondrial outer membrane. The design of fullerene glutathione adenosine phosphate allows it to control ROS release through porins, as well as to help depolarize the over polarized mitochondria in autistic neurons by assisting with the charge transport into and out of the mitochondrial porins.

Figure 12:
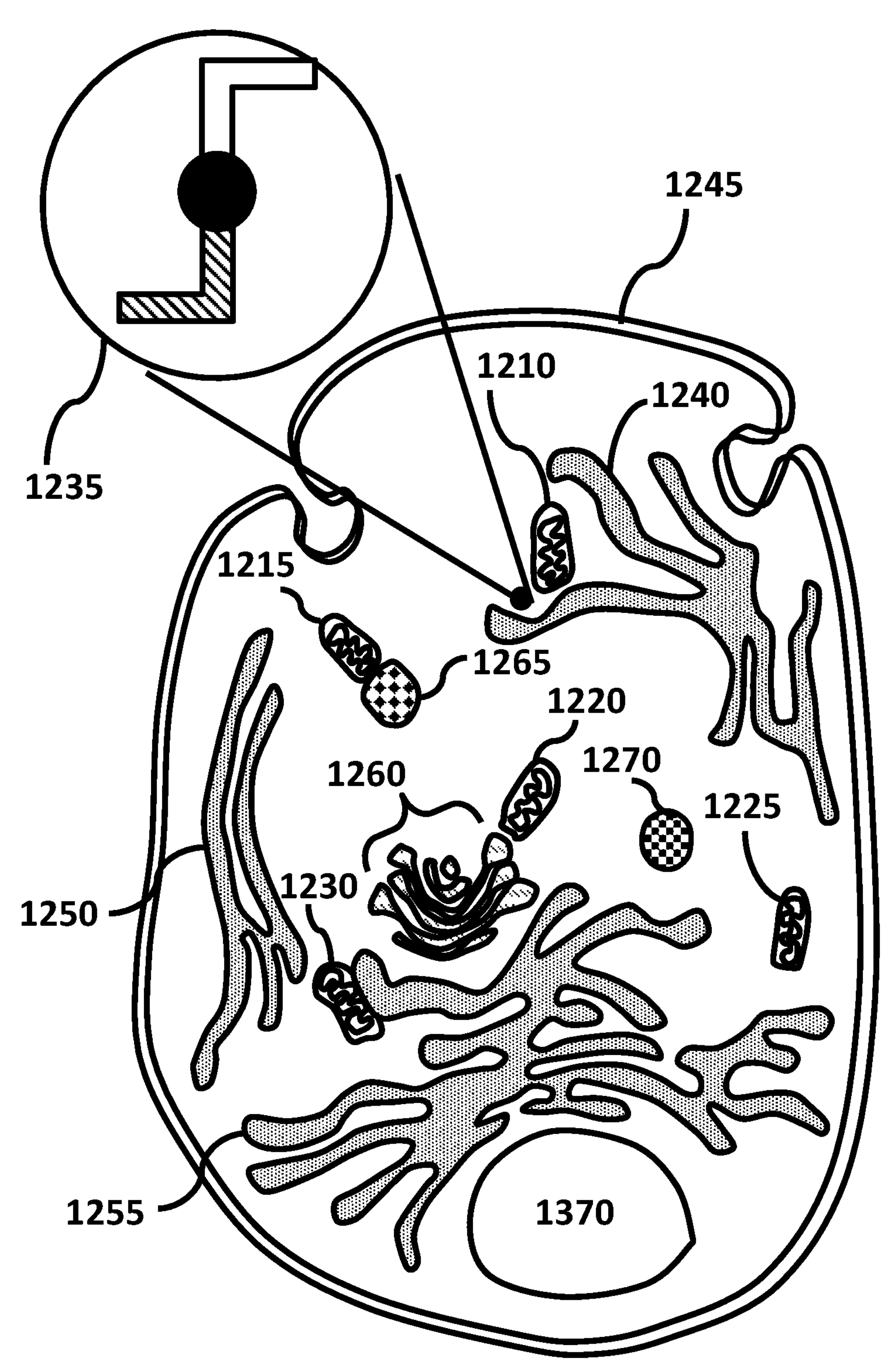
FIG. 12 is an illustration of cell organelles in proximal abutment with a multiplicity of mitochondria provided with dual neurotransmitter C60-GSH-ATP nanoparticles.

FIG. 12 illustrates organelles of mitochondrial associated membranes (MAM), where the distance between proximal abutting mitochondria 1210, 1215, 1220, 1225, 1230 and organelle structures is about 90 nanometers during the cellular process of catabolism or anabolism. Expanded inset 1235 contains the icon symbol representing a fullerene adenosine phosphate glutathione dual neurotransmitter nanoparticle or any of its metabolites. One or more of such molecules are interposed in the gap region between mitochondrion 1210 and the endoplasmic reticulum (ER) 1240 structure to which it proximally abuts. The illustrated portion of neural or somatic cell 1245 includes the endoplasmic reticulum 1240, 1250 and membranes 1255 associated with the cell nucleus, the Golgi complex 1260, and lysosomes 1265, 1270 which are organelles that can at any time come into similar proximal abutting contact with mitochondria. Such contact of mitochondrial associated membranes (MAMs) is for the purpose of exchanging signaling molecules, anions, and cations as well as for performing exchange of energy by hydrogen and electron transfer which enables cellular respiration. The role of the C60-GSH-ATP nanoparticle ensemble is to expedite such signaling and ion trafficking, help to regulate mitophagy, to restore calcium and proton ion homeostasis, reduce mitochondrial oxidative stress, and to improve efficiency of the generation of adenosine triphosphate by the electron transfer cycle (ETC). The intent of the C60-GSH-ATP nanoparticles having dual neurotransmitters is to help regulate each of these metabolic processes. The storage of charges helps to regulate charge distribution and thereby improves the state of homeostasis of the mitochondrial membrane polarization. Especially the mitochondria in the ocular cornea are expected to benefit from these nanoparticles enhanced ion shuttling ability to loosen and remove protein deposits leading to cataracts. The defects of lysosomal protein catabolism in lysosomes 1265, 1270 can be reworked using the nanoparticles. In several aspects, the C60-GSH-ATP is designed to improve the function and structural characteristics of the MAMs. This will become a useful treatment in autism and may find use in other types of neuropathies and channelopathies that can benefit from the promotion of electron and proton shuttling to help overcome a range of charge transport defects.

Figure 13:
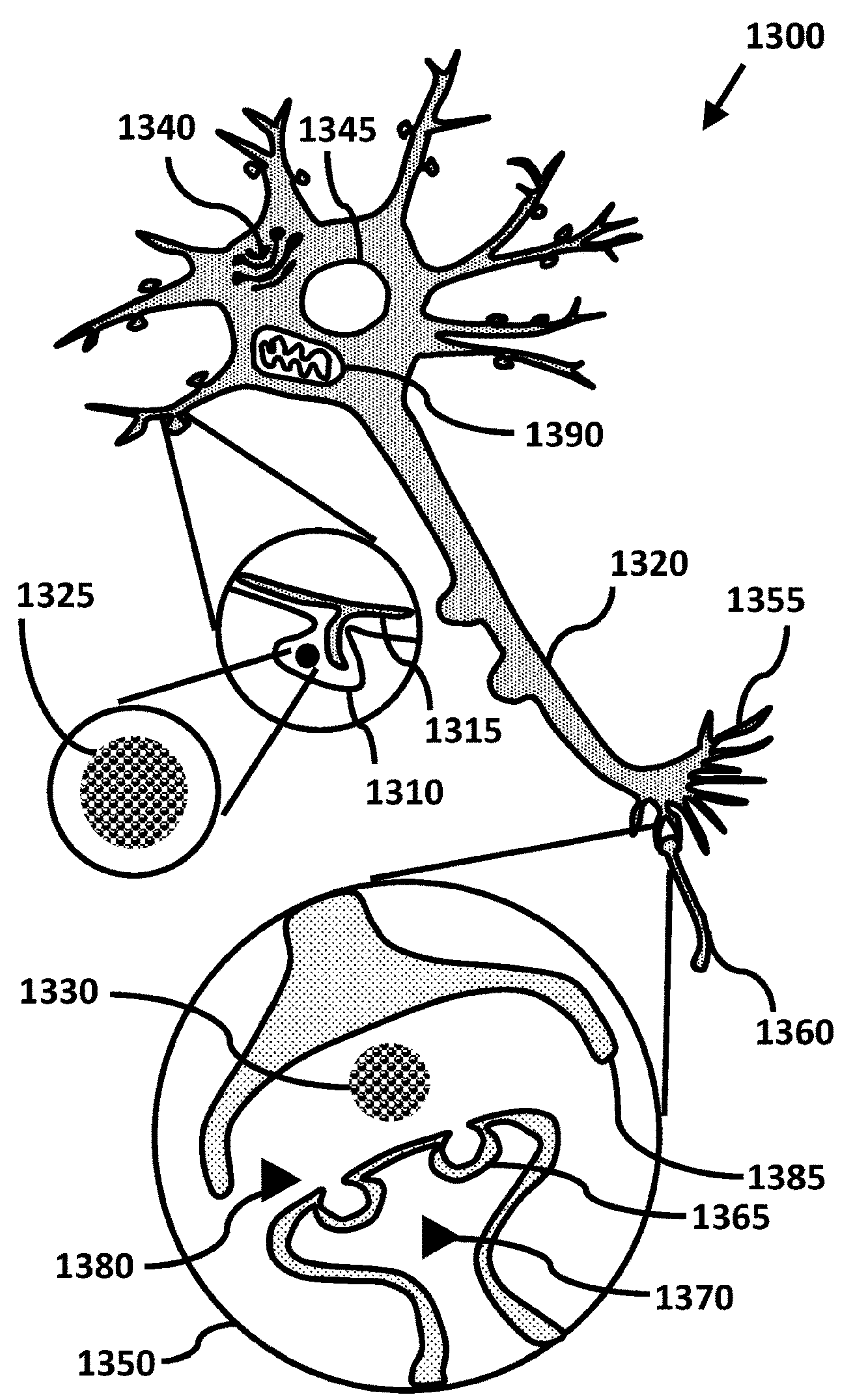
FIG. 13 is an illustration of a neuron provided with dual neurotransmitter C60-GSH-ATP nanoparticles.

FIG. 13 illustrates neuronal cell 1300. A dendrite, 1310 is illustrated in the circled expanded inset view; this view also illustrates endoplasmic reticulum (ER) 1315 extending throughout the cell cytosol where it is bounded by the cell plasma membrane (PM) 1320. The ER is in physical proximity with the plasma membrane to expedite lipid transfer, Ca2+ ion homeostasis, and synaptic plasticity. The nanoparticle ensemble of C60-GSH-ATP 1325, 1330 helps to shuttle anions and cations through the cytosol and across organelles and membranes. Vesicles originate at the Golgi apparatus 1340 to transport lipids, calcium and other cations, hydrogen protons, electrons, and cellular signaling molecules such as sirtuins (not shown). In autism and other neuronal pathologies, effective transport of critical cellular materials from the cell nucleus 1345 and the Golgi apparatus via the ER to the plasma membrane can become compromised. The interposition of the dual neurotransmitter nanoparticle composition, fullerene glutathione adenosine phosphates can facilitate the transport of such cellular materials including electrons and protons between the ER 1315 and the plasma membrane 1310 to restore and remediate functional neuronal processes in neurons. Another expanded view, 1350 illustrates a synapse at the junction of a first neuron 1355 and a second neuron 1360. The presynaptic bouton 1365 releases neurotransmitters 1370, 1380 into the synaptic cleft. The post synaptic neuron 1385 accepts the ionic and electrical signals provided by the presynaptic neuron that are conveyed in part by the released neurotransmitters 1370, 1380. The nanoparticle ensemble of C60-GSH-ATP helps to shuttle anions and cations across the synaptic cleft to accommodate deficits in bioenergetic signaling ability arising from the neural mitochondria 1390.

Figure 14:
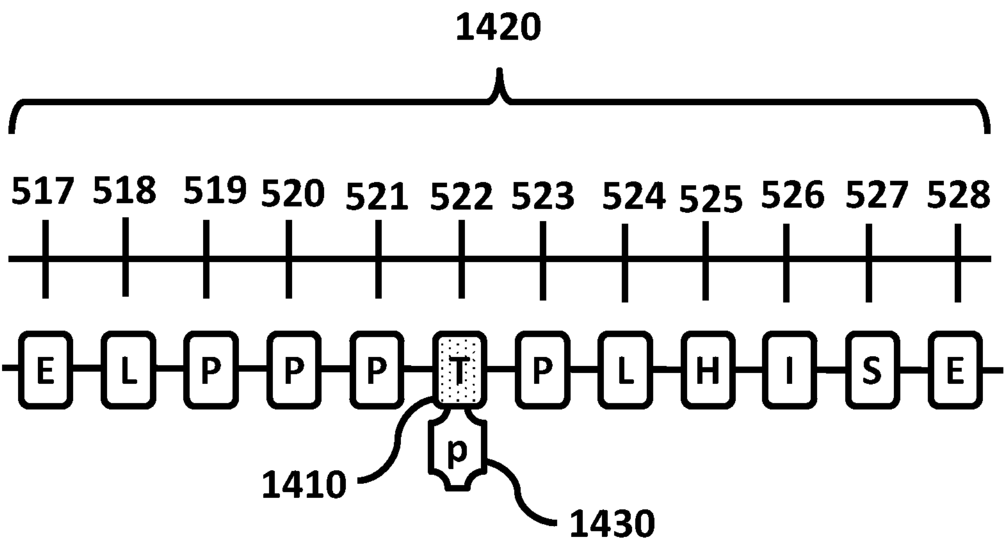
FIG. 14 is an illustration of an allosteric portion of the sirtuin 1 molecule with a mineral phosphate and the same region on sirtuin 1 being multiply adducted using C60-GSH-ATP.
Figure 14:
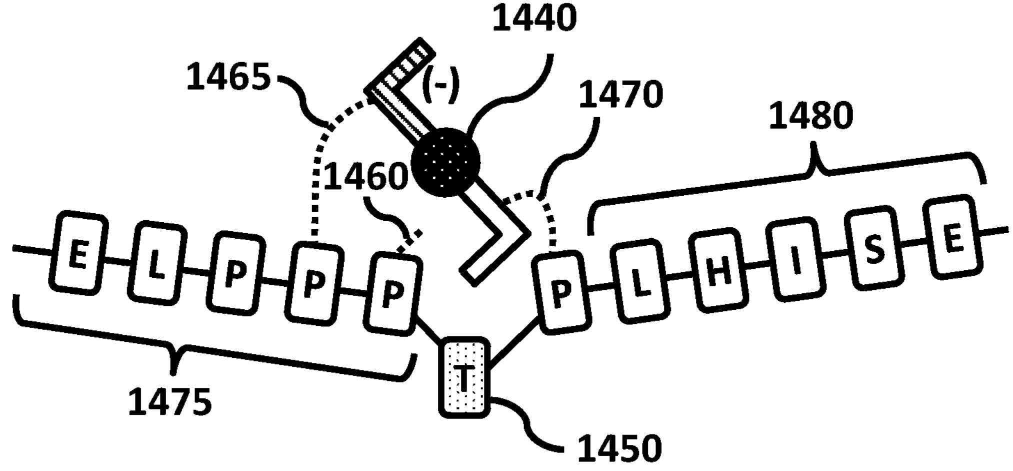
Figure 15:
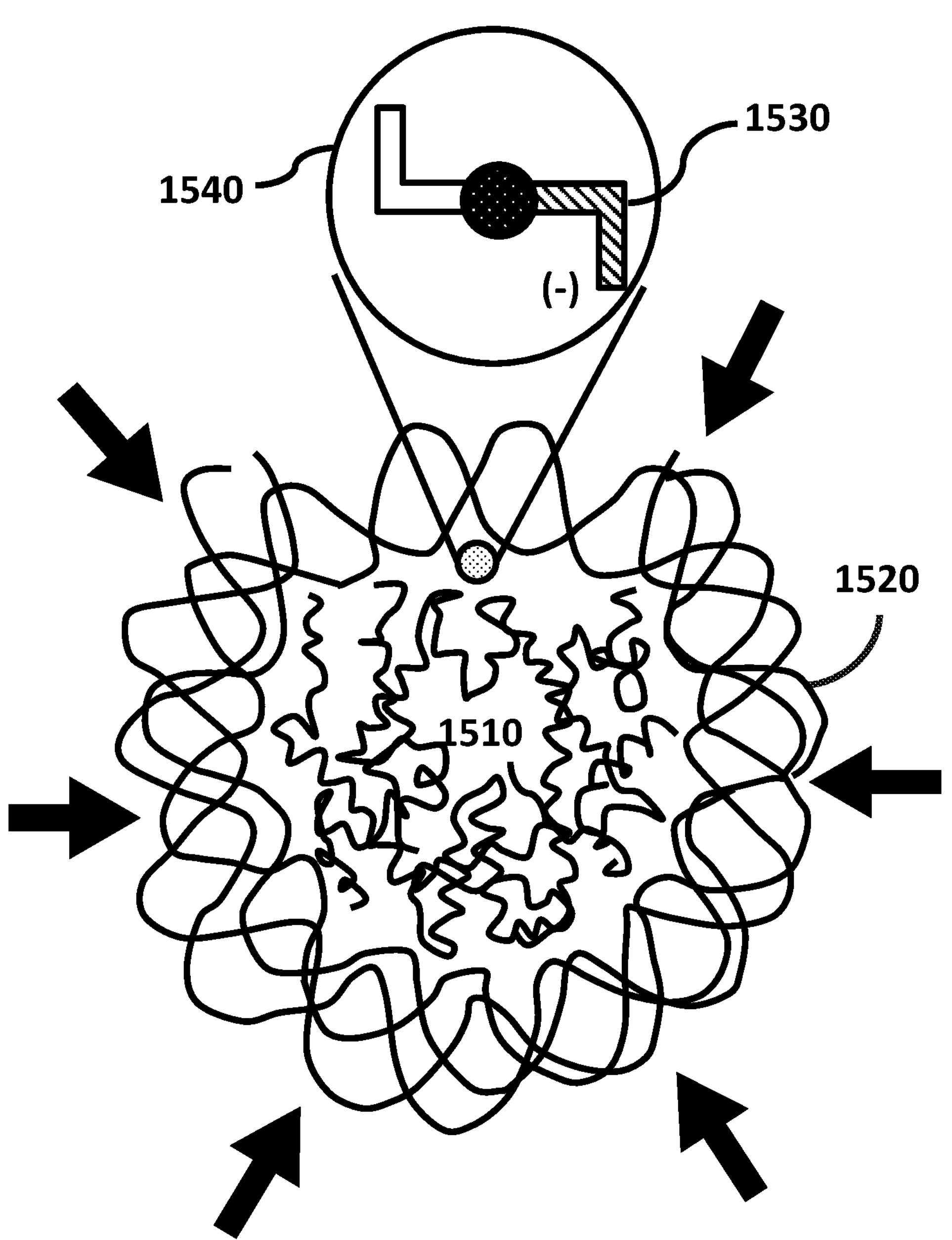
FIG. 15 is an illustration of the direction of increased DNA binding on chromatin having reversibly silenced genes on treatment with the nanoparticle composition.

FIG. 14 illustrates an allosteric portion of enzyme sirtuin-1. The allosteric region 1410 is a location on a section of the molecule of enzyme sirtuin-1 where amino acid locations 517 to 528 are numbered by the reference line with tick marks indicated within the bracketed region 1420. Histone deacetylase type III sirtuin-1 location 522 is a tyrosine amino acid 1410 which has undergone phosphorylation at the allosteric site, as indicated by phosphorylation symbol 1430. Such phosphorylation alters the conformation or shape of sirtuin-1 to enable a significant improvement in the catalytic deacetylase function of this enzyme. Excessive acetylation and acylation in autistic neurons because of the high load of ROS in ASD is underappreciated. Therefore, increasing the function of sirtuin-1 as one way to help bring back cellular homeostasis to allow repair and proper development of the affected brain tissues. Other allosteric locations also exist both on the illustrated sirtuin-1 and the other sirtuins, of which 7 are known at present, as well as on many other types of enzymes that function as regulatory molecules. Phosphorylation by inorganic phosphate group 1430 is only one type of a phosphate adduct that may bind with tyrosine at location 522 on sirtuin-1. Fullerene glutathione adenosine phosphate (FGAP) 1440 is illustrated to have phosphorylated tyrosine at location 522 of a sirtuin-1 at 1450, wherein this allosteric site phosphorylation is accompanied by a multiplicity of hydrogen bonds 1460, 1465, 1470 that enable far greater conformational change in sirtuin-1 shown by the bent conformation of regions 1475, 1480 than is possible by native cellular phosphates. This action serves to stabilize the enhancement of deacetylase enzymatic activity, which then proceeds through a cascade of signaling molecules to deacetylate chromatin histones at the cell nucleus, as illustrated in FIG. 15. The utility of the artificial phosphorylation molecule fullerene adenosine phosphate glutathione, inclusive of variations being triphosphate, diphosphate, monophosphate, and cyclic monophosphate adenosine metabolites, and of monomeric reduced and dimeric oxidized glutathione, is designed to improve histone deacetylase enzyme catalytic function, to treat autism, and to assist with the signaling function of SIRT1 to initiate DNA repair in brain cells chronically exposed to DNA damage by ROS.

FIG. 15 illustrates the direction of increased DNA packing and binding on chromatin. The direction of cooperative shrinkage facilitated by mutual molecular associations is illustrated by multiple black arrows pointed to central histones of the chromatin spool 1510, around which is wrapped multiple windings of the double stranded helix of deoxyribonucleic acid (DNA) 1520 having multiple silenced genes on treatment with multiple fullerene glutathione adenosine phosphates (FGAP) 1530 represented in the enlarged inset view 1540. Multiple FGAP 1530 can have both positive and negative charged ends, where the positive end is attracted to form counter-ionic bonds with the negatively charged phosphate bridges of the central ladder regions of DNA 1520, and the negative end of FGAP 1530 can be attracted to the exposed amine functional groups of deacetylated histones in the chromatin molecular spool 1510 located within the cell nucleus. It is noted that the histones on the chromatin spool 1510 may become deacetylated by histone type III deacetylases or sirtuins, especially allosterically activated SIRT1 where a section of this class of enzyme is illustrated in FIG. 14. Multiple hydrogen bonds are formed between abutting structures in DNA 1520 and the deacetylated positively charged chromatin histones 1510, where this process is facilitated by the interposition of a multiplicity of FGAP 1530 to stabilize the silencing of a multiplicity of undesirably expressed gene segments from transcriptional expression within and among ROS damaged DNA 1520, thereby collectively stabilizing the genome of the affected individual, and halting the expression of misfolded proteins and nonfunctional protein segments from at least some of the DNA in autistic brains.

Figure 16:
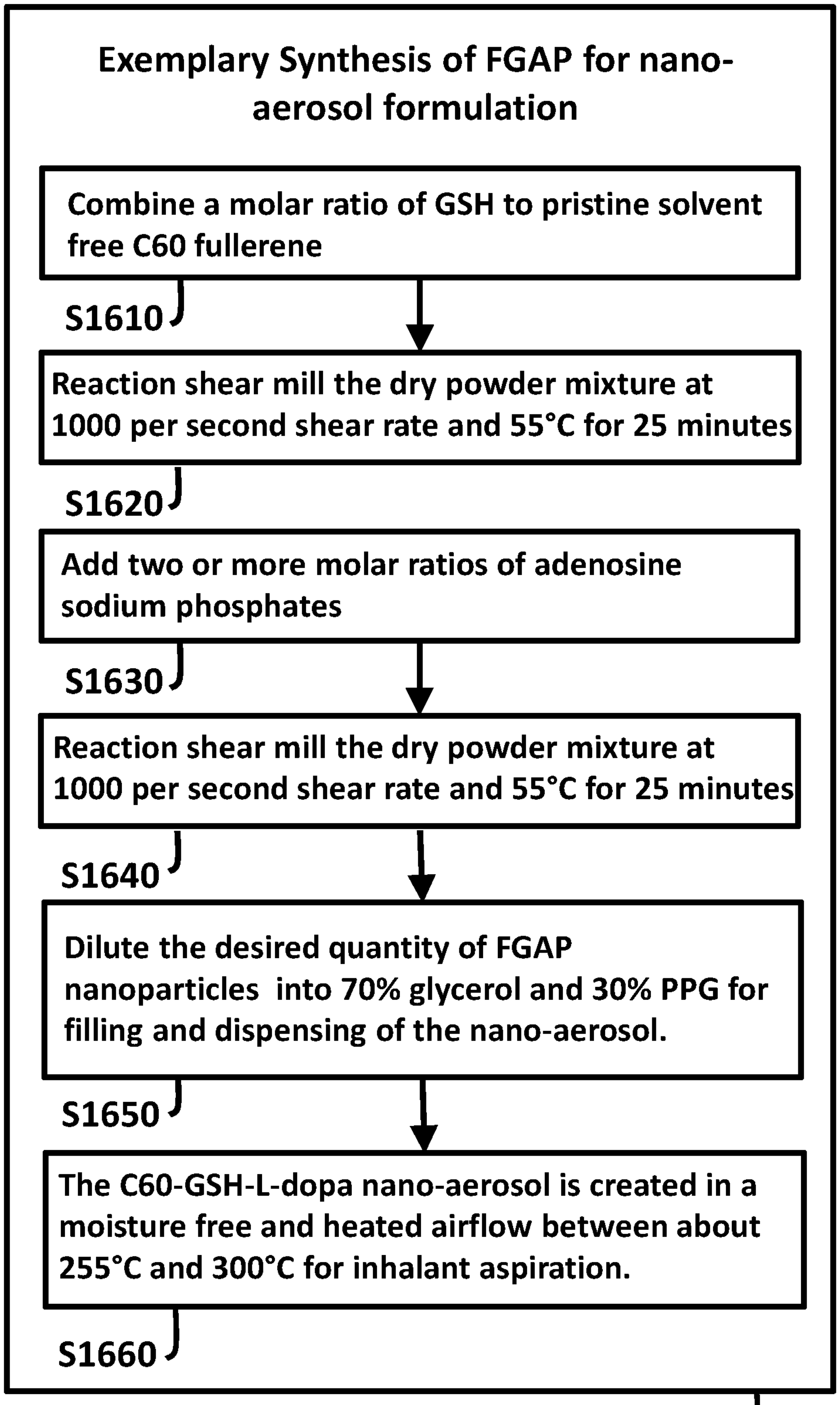
FIG. 16 is an illustration of an exemplary fullerene ATP-GSH synthesis.

FIG. 16 illustrates a flow chart of fullerene glutathione adenosine phosphates (FGAP) exemplary synthesis S1600. In step S1610, 1 mole of C60 is combined with 1 mole of reduced glutathione. In step S1620, the dry powder mixture is reactive shear milled for about 25 minutes, taking care not to exceed about 55° C. to avoid glutathione oxidation or decomposition. In step S1630, about two or more molar ratios of adenosine phosphates are added to this mixture. The preferred additive is adenosine tri-phosphate, however other adenosine phosphates are allowed, because the cellular metabolism will facilitate the metabolic interconversion of adenosine phosphates by the addition or loss of a phosphate group, as illustrated in FIG. 3. In step S1640, a reactive shear mixing process is performed at about 1000/second shear rate to the combined mixture for about 15 minutes, taking care not to exceed about 55° C. to avoid functional group decomposition. In step S1650, the desired quantity of FGAP nanoparticles is diluted into a mixture of 70% glycerol and 30% PPG for filling and dispensing of the nano-aerosol. In step S1660, the dissolved nano-aerosol fluid product of fullerene glutathione adenosine phosphates is transferred into a device made for e-vapor fluid dispensing and nano-aerosol administration.

Figure 17:
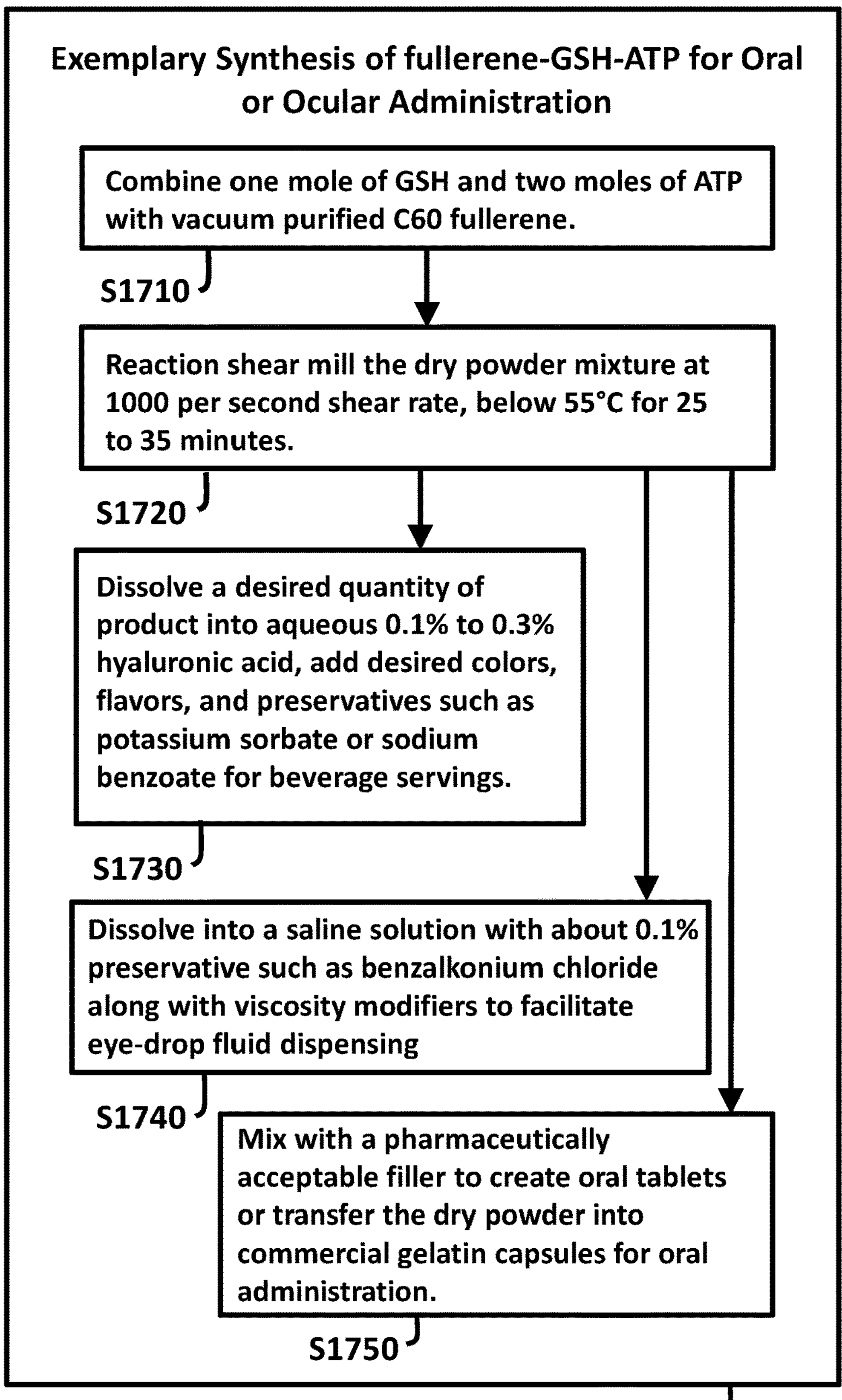
FIG. 17 is an illustration of an exemplary fullerene GSH-ATP synthesis.

FIG. 17 illustrates a flow chart of fullerene glutathione adenosine phosphates (FGAP) exemplary synthesis for oral solutions S1700. To begin in step S1710, one mole of pristine, vacuum purified C60 carbon fullerene is added to one mole of reduced glutathione and 2 moles of adenosine triphosphate. In step S1720, a shear mixing reaction process is performed at about 1000 per second shear rate for 25 to 35 minutes, taking care not to let the mixture exceed about 55° C. to avoid GSH oxidation or ATP decomposition. One of these alternative steps then takes place. In alternative step S1730, the reaction product of fullerene glutathione adenosine phosphates is dissolved into water containing at least about 10% glycerol to create an oral solution, or a water based topical solution that can be applied to the skin. In alternative step S1740 the reaction product of fullerene glutathione adenosine phosphates is dissolved into a saline solution with about 0.1% of a preservative, such as benzalkonium chloride, along with any viscosity modifiers needed for eye-drop fluid dispensing. Or, in alternative step S1750, the milled powder is mixed with a pharmaceutically acceptable filler and formed into oral tablets, or disposed into commercial gelatin capsules, for oral administration.

Figure 18:
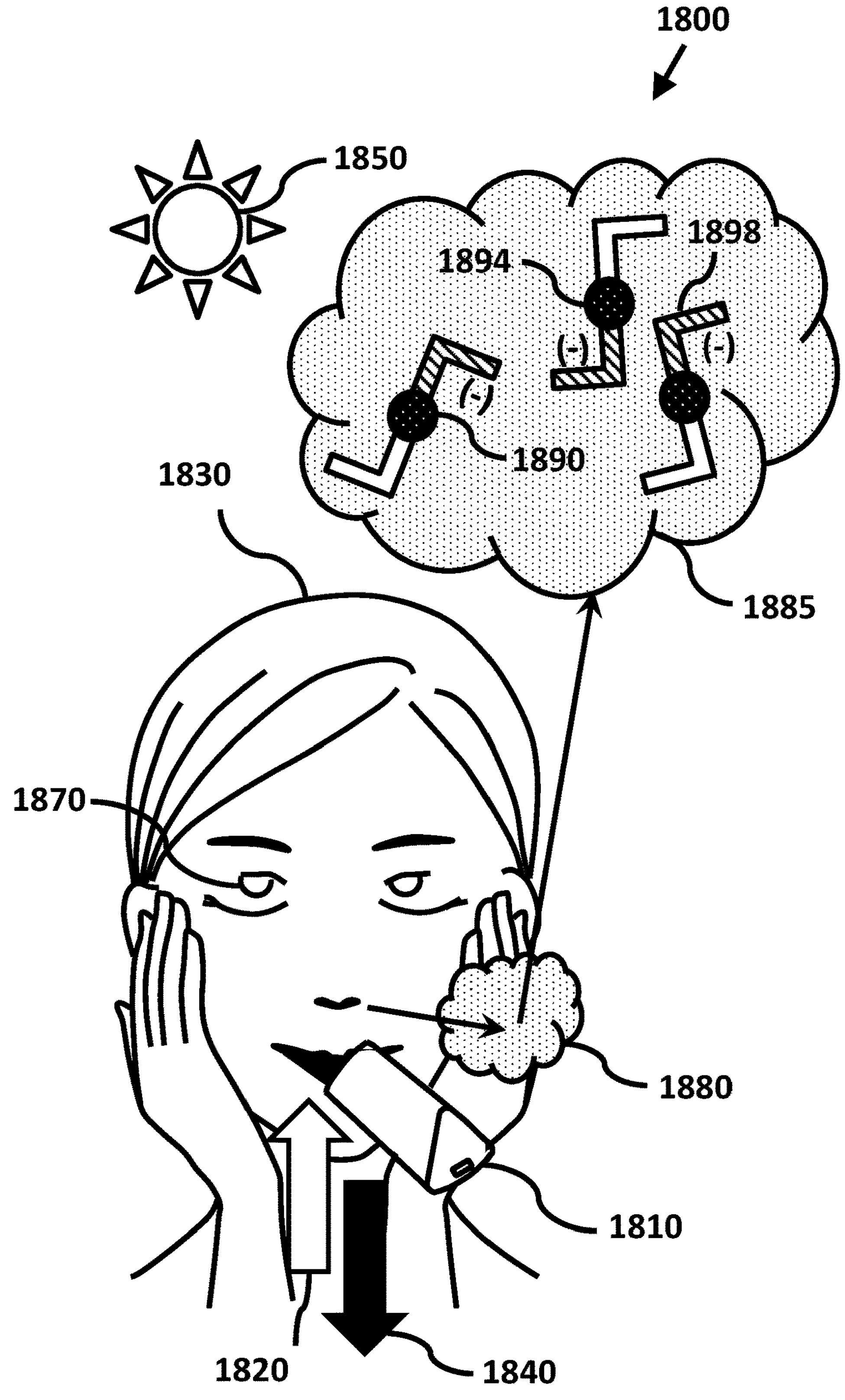
FIG. 18 is an illustration of the method of thermally aerosolizing a vapor inhalant for self-administration.

FIG. 18 illustrates some exemplary methods of use 1800 of fullerene-GSH-ATP (FGAP). Fullerene glutathione adenosine phosphate nanoparticles in a fluid solution are charged into a cartridge for an electronic vapor generation device 1810. Large white arrow 1820 indicates the nano-aerosol is being aspirated or breathed in by patient or user 1830 into the airways and lungs. In a second method of use, large black downward arrow 1840 serves to indicate the oral administration of the dual neurotransmitter FGAP being swallowed as an ingestible solution or oral tablet as it travels in the direction of the esophagus to the region of the stomach and into the digestive system. The improved cognitive effect of FGAP on the brain of autistic patients results from the nano-aerosol administration of this dual neurotransmitter ensemble. In yet another embodiment, the administration to the eye of FGAP is performed by the physical application of eye drops to treat cataracts of the eye 1870, or to serve as an administration of treatment of FGAP for Autism to treat neurocognitive deficits.

Yet another method of use is illustrated by the exhalation of FGAP as smoke puffs exhaled out of the nose and airways as indicated by the two narrow black arrows and the cloud shaped exhaled vapors 1880, 1885 to contain the schematically symbolized FGAP nanoparticles, 1890, 1894, 1898. Systems that may be used for the method of dispersion of the FGAP represented by a dispenser 1810, include, without limitation, any of the electronic cigarette devices produced internationally and listed in Appendix 4.1, "Major E-cigarette Manufacturers" of the "2016 Surgeon General's Report: E-Cigarette Use Among Youth and Young Adults" published by the Center for Disease Control and Prevention (CDC), Office of Smoking and Health (OSH) freely available at the CDC.GOV website, or any combination of piezoelectric, resistively heated, or inductively heated vaporized fluid delivery methods that can be utilized to deliver the composition of the present invention, especially when approved as a medical drug delivery device. Each embodied variation of such methods without limit are intended to aspirate aerosols as the method of therapeutic substance delivery of the composition of the present invention directed into the nasal cavities, mouth, tracheal breathing orifice, or intubated trachea of a patient. The supply direction of nebulized feed of FGAP on inhalation and exhalation are delivered into the airways and lungs of the intended patient by the flow of supplied air as indicated by the direction of upward and downward facing large arrows 1820, 1840.

In summary, any of the fullerene glutathione adenosine phosphate variations or their metabolites, or mixtures thereof, may comprise the nanoparticulate composition used in the embodiments of the present invention, as a vapor inhalant, or as a topical cream, or as an orally ingested solution, as an orally ingested tablet or capsule, or as an eyedrop medication.

Figure 19:
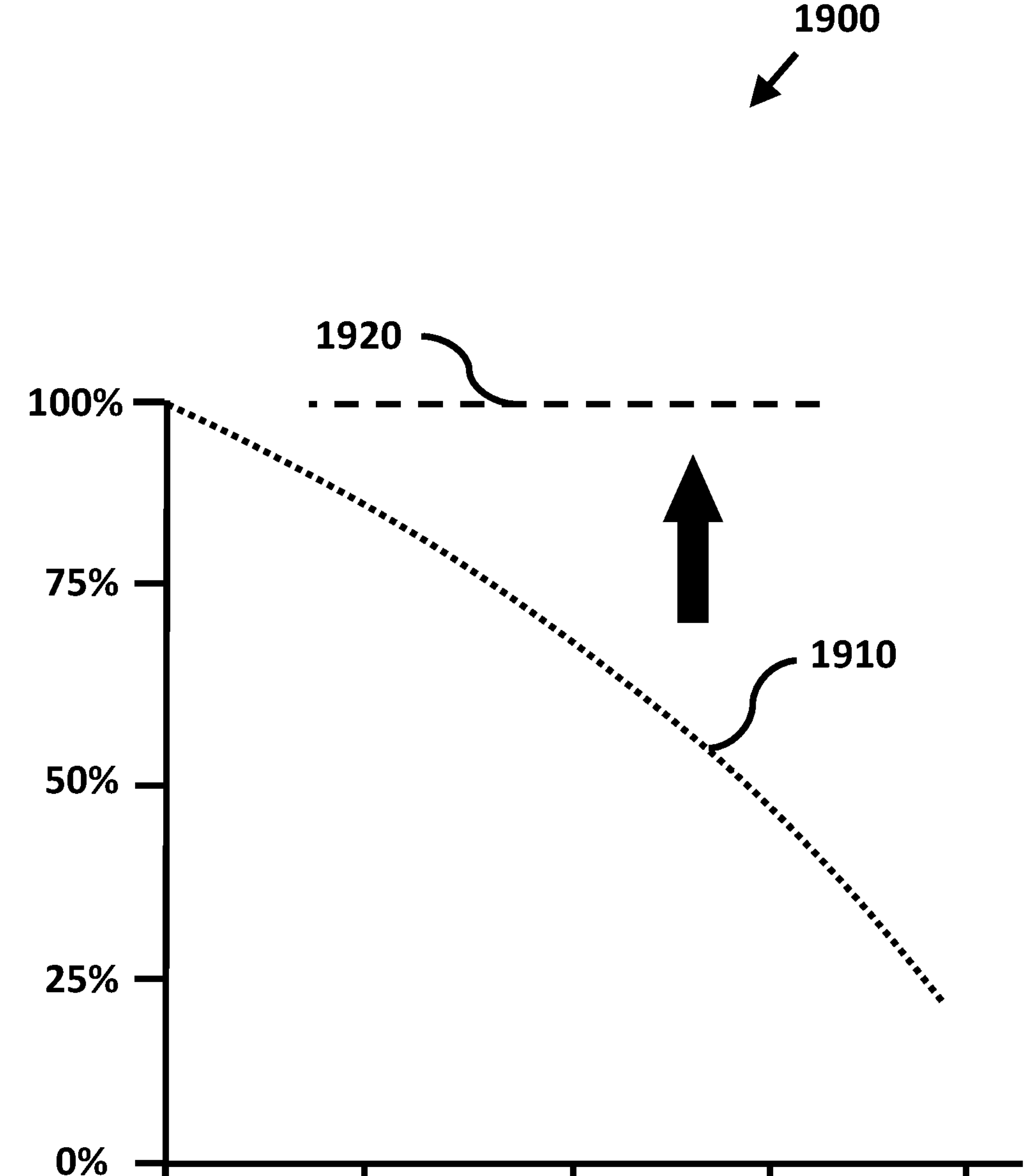
FIG. 19 is an illustration of normalized bioenergetic data based on cytochrome c oxidase (COX) concentration in blood plasma with age during a human lifetime.

FIG. 19 illustrates a normalized data graph 1900 of typical cytochrome c oxidase concentration, where this protein is also known as 'Complex IV' or COX. COX is associated with bioenergetics effectiveness because it is the last enzyme in the respiratory electron transport chain (ETC) of mitochondria in cells. COX concentration is deficient in the brain cells of many persons who have the autism spectrum disorder. This is because autism is a metabolic deficit that leads to cognitive deficits, where the brain is the largest consumer of metabolic energy. COX is located within the cell membrane, where it functions to convert molecular oxygen to two molecules of water by the transfer of 4 electrons combined with four protons from the cell cytosol or inner aqueous phase to make two water molecules. Neurons rely on oxidative phosphorylation by COX for energy and to produce their electrical potentials. Dotted line 1910 represents the percentage decline of COX in human beings from birth over the span of a typical human lifetime. The human lifetime in number of years lived is the x-axis, and the percentage of COX concentration is the y-axis in this graph. The COX decline is greater for those with metabolic disease or congenital bioenergetic deficits as present with autism spectrum disorder. One objective of the fullerene glutathione adenosine phosphates of the present invention is to restore or enhance as much as possible of the bioenergetic capability of COX, using a cascade of signaling molecules via enzyme activation, as indicated by the upward direction of the large black arrow pointing toward dashed line 1920.

Figure 20:
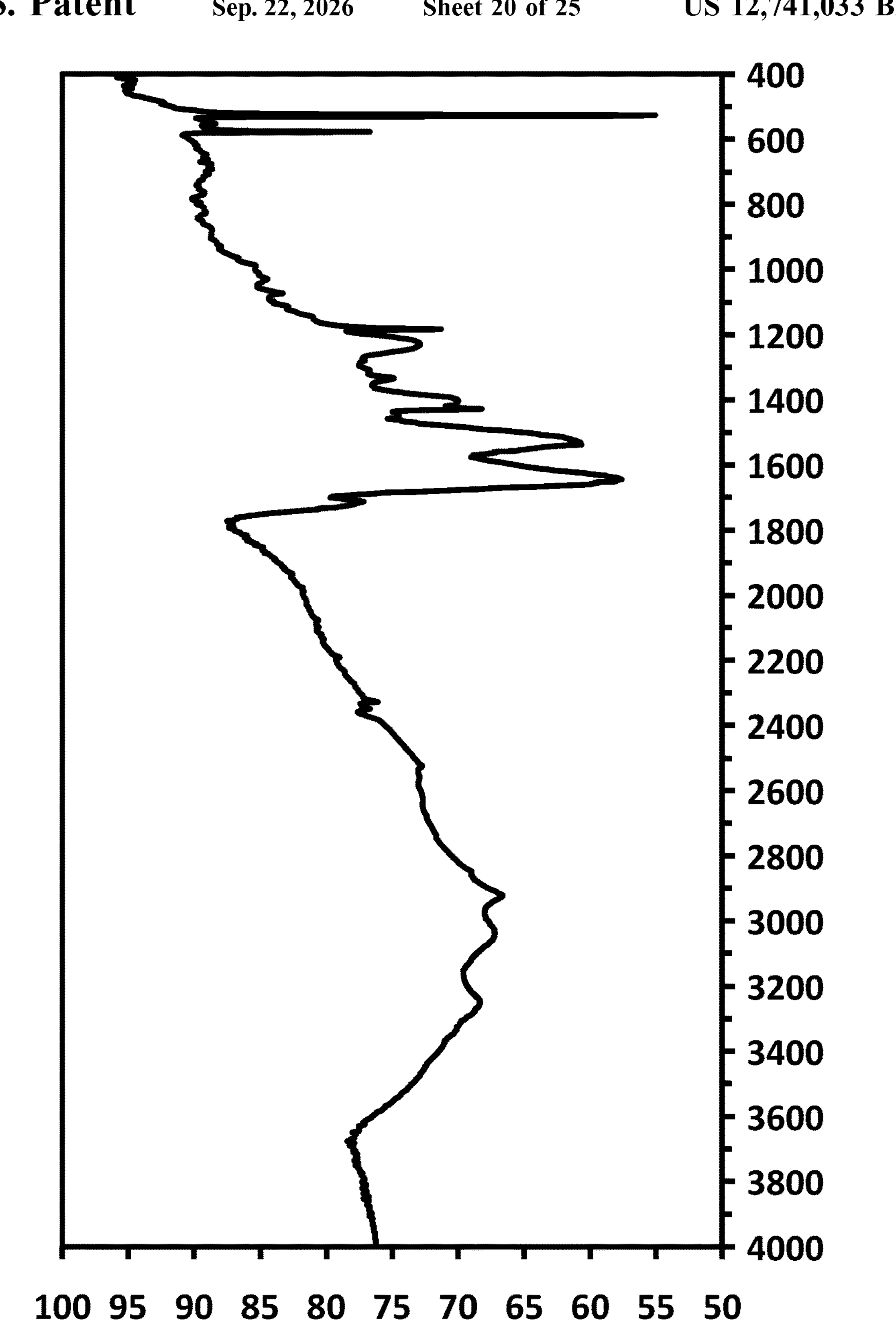
FIG. 20 is an illustration of experimental FTIR data for C60-GSH.

FIG. 20 illustrates the FTIR data for C60-GSH. All the Fourier transform infra-red (FTIR) spectrographs hereinafter were measured by transmittance using the potassium bromide (KBr) compressed flow solid pellet compact preparation method. The material used for analysis was obtained by the method of mixing, crushing, and consolidating under 7 metric tons of pressure, about 0.001 grams of the analyte substance with 1 gram of a diluent solid KBr that is substantially transparent to infrared light, and which flows under pressure to form a translucent pellet of about 0.4 mm thickness. Spectral background subtraction in air using a control pellet of the same mass and thickness having pure KBr was used to obtain a baseline instrument infrared spectral response. This method is generally referred to as the 'KBr pellet' sample preparation method, and it is used hereinafter throughout for each FTIR experimental data collection and spectral analysis. The Fourier transform infrared spectrophotometer used herein to obtain FTIR spectra throughout, is a model RF6000 FTIR instrument manufactured by Shimadzu of Japan. Each FTIR data graph hereinafter is provided with a numeric scale ranging from 400 to 4000 to represent reciprocal centimeters or ($cm^{-1}$) in wavenumbers.

The C60-GSH numeric scale ranging from 50 to 100 represents percentage transmittance and has units of %. It is notable that the typical reduced glutathione sulfhydryl (S—H) peak is not observed at 2523 $cm^{-1}$, indicating the sulfur-hydrogen stretch has disappeared because of a chemical reaction of GSH, likely with C60, which supports the molecular sulfur binding reaction. Notable also are the very strong and sharp C60 fullerene aromatic carbon-carbon stretching bands at 576 $cm^{-1}$ and 526 $cm^{-1}$. The peak at 3252 $cm^{-1}$ is attributed to the nitrogen stretch of a primary amine group in the glutathione adduct. The peak at 1644 $cm^{-1}$ is attributed to the carbonyl (C═O) group of glutathione. Sharp C60 fullerene aromatic carbon-carbon stretching bands appear at 576 $cm^{-1}$ and 526 $cm^{-1}$.

Figure 21:
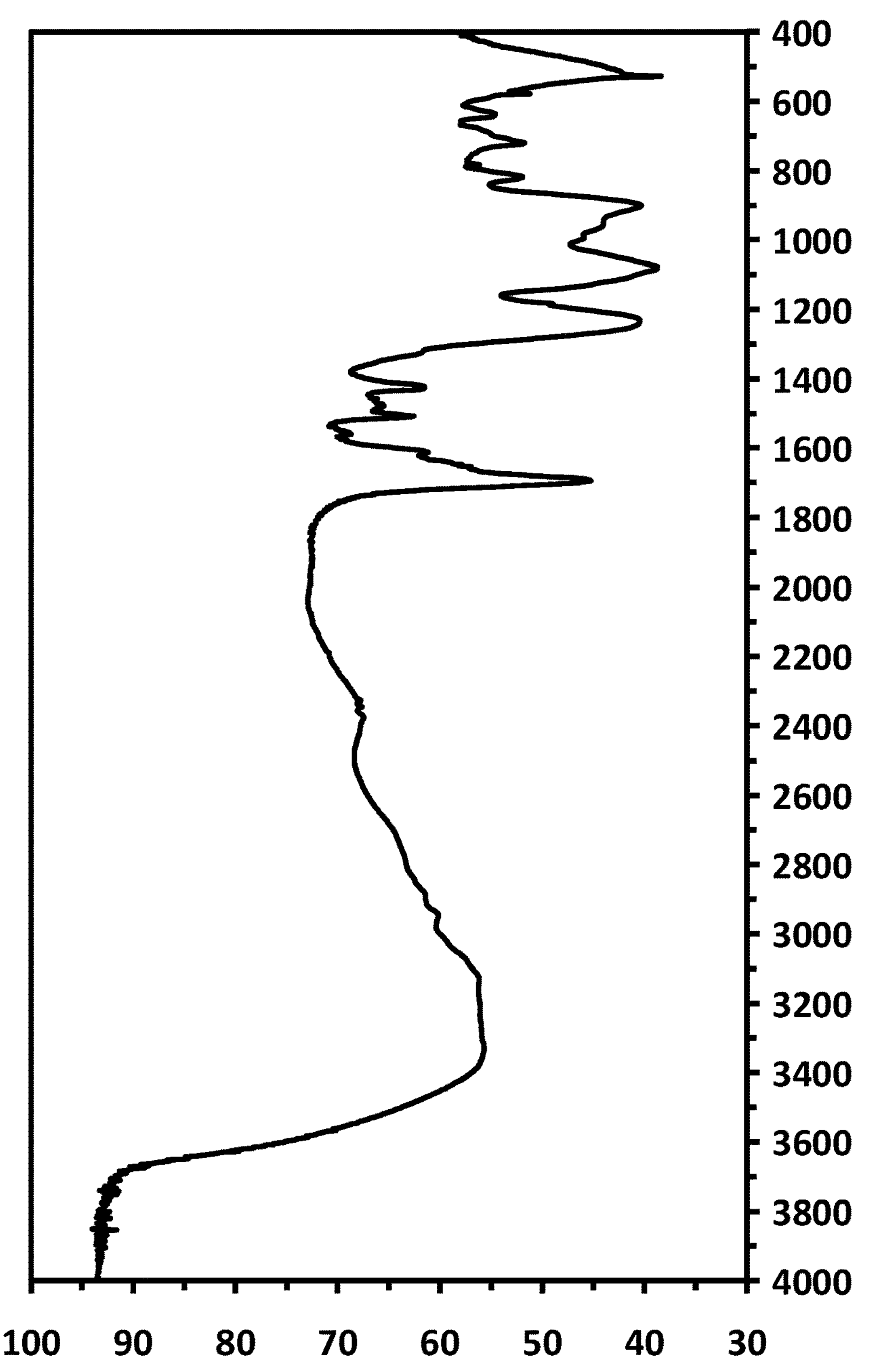
FIG. 21 is an illustration of experimental FTIR data for C60-ATP.

FIG. 21 illustrates the FTIR data for C60-ATP. The numeric scale ranging from 30 to 100 represents percentage transmittance and has units of %. The broad absorbance band from 3650 $cm^{-1}$ to 2600 $cm^{-1}$ is attributed to an additive combination of contributions from the hydroxyl groups of phosphates, and the ring nitrogen stretching vibrations from within the adenosine ring structure. The absorbance peak at 1694 $cm^{-1}$ is attributed to a vibration from double bonded phosphorus to oxygen (phosphonyl or P═O) functional groups. The easily recognized sharp C60 fullerene aromatic carbon-carbon stretching bands appear at 576 $cm^{-1}$ and 526 $cm^{-1}$. The absorbance at 1077 $cm^{-1}$ is attributed to carbon-oxygen ring vibrations in the adenosine functional group.

Figure 22:
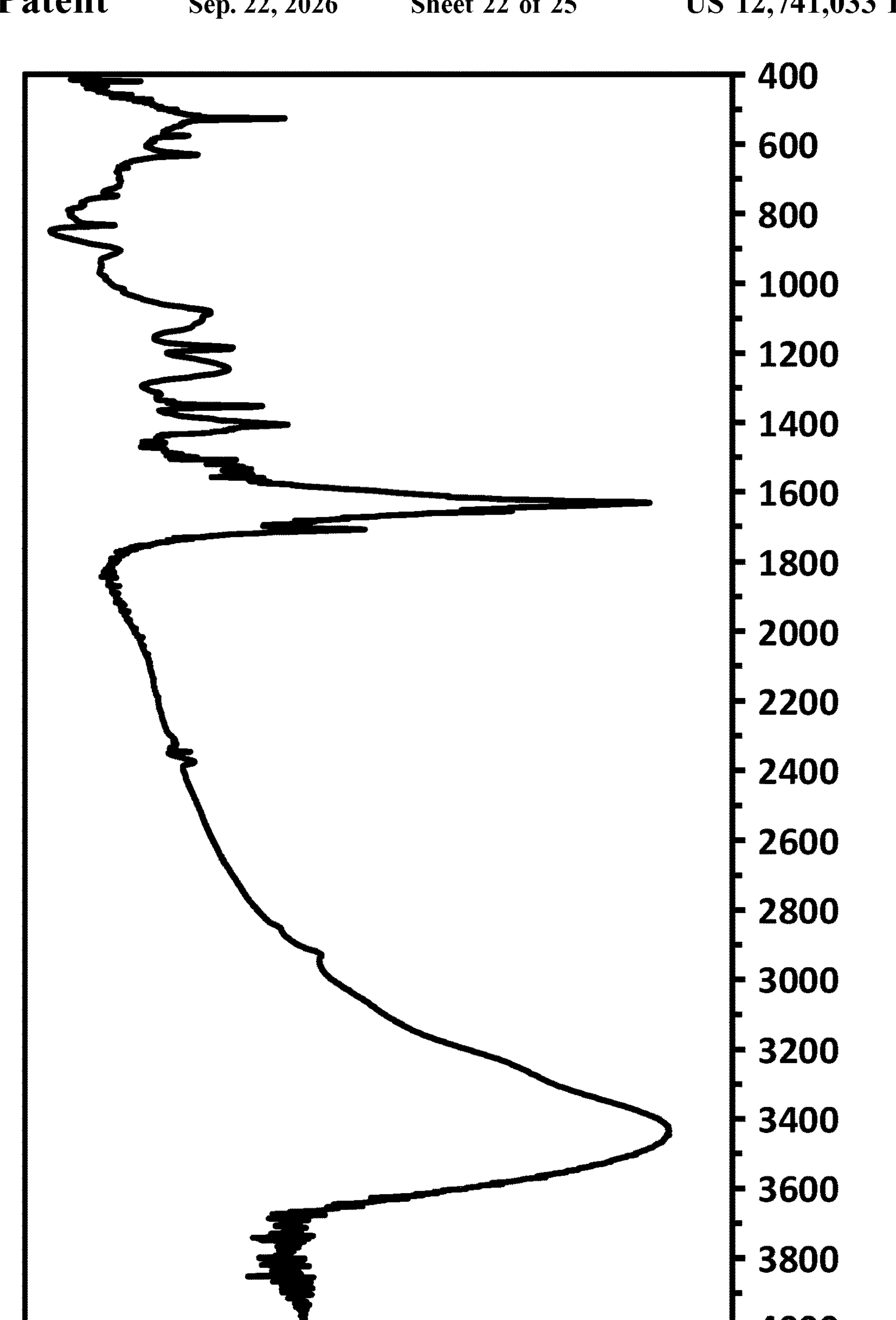
FIG. 22 is an illustration of experimental FTIR data for C60-GSH-ATP dual neurotransmitter nanoparticle ensemble.

FIG. 22 illustrates the FTIR data for the C60-GSH-ATP dual neural transmitter nanoparticle ensemble. The absorbance at 1632 $cm^{-1}$ is attributed to at least one carbonyl bond that may belong to either the ATP group or the GSH group, and likely represents a sum of interactive absorbances from both functional groups. The easily recognized sharp C60 fullerene aromatic carbon-carbon stretching bands appear in this data at 576 $cm^{-1}$ and 526 $cm^{-1}$. Many of the lesser absorbance bands are attributed to a confluence of those fingerprint absorbances seen for C60-ATP and C60-GSH. Overall, this FTIR spectrum is consistent for the type of absorbances that are to be expected for an achieved chemical structure of the C60-GSH-ATP dual neurotransmitter nanoparticle, in accordance with these teachings.

Figure 23:
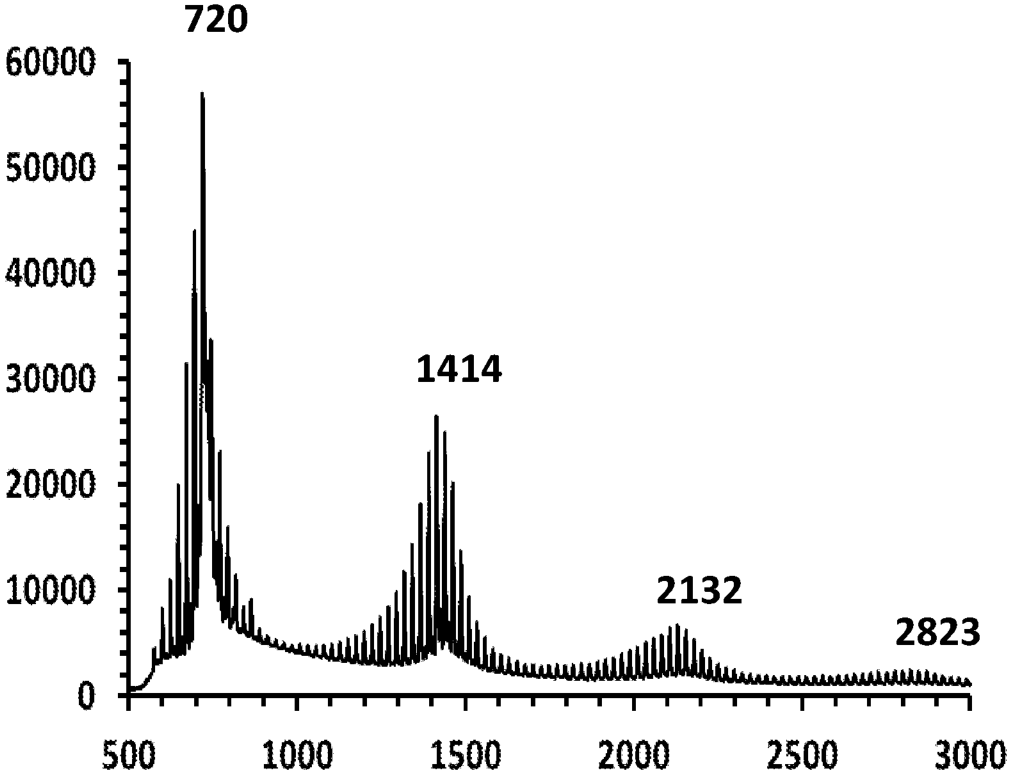
FIG. 23 is an illustration of experimental mass spectrograph data for C60-ATP.

FIG. 23 illustrates the negative mode MALDI-TOF mass spectrograph data of adenosine triphosphate derivatized fullerene (C60), being C60-ATP. This sample, as well as each of the subsequent MALDI-TOF experimental test results hereinafter, was introduced for test by laser vaporization into a Voyager Mass Spectrograph from Applied Biosystems (Foster City, California, USA). Negative mode bombardment was by fast moving electrons at about 70 eV energy. This resulted in molecular fragmentation and electron removal from the highest molecular orbital energy as molecular ions were formed. The ratio of mass to charge (m/z) is used to determine the molecular ion fragments to help determine the pieces of the original molecule in this assay.

The largest molecular peak at 720 mass-to-charge ratio represents the core molecule of C60. The grouping of peaks at mass-to-charge ratio of 1414 represents the molecular fragments associated with one adenosine triphosphate group functionalized to one fullerene molecule as the primary reaction product. The grouping of peaks at mass-to-charge ratio of 2132 represents the minor amounts of molecular fragments associated with two adenosine triphosphate groups functionalized to one fullerene molecule. The grouping of peaks at mass-to-charge ratio of 2823 represents the trace amounts of molecular fragments associated with three adenosine triphosphate groups functionalized to one fullerene molecule.

Figure 24:
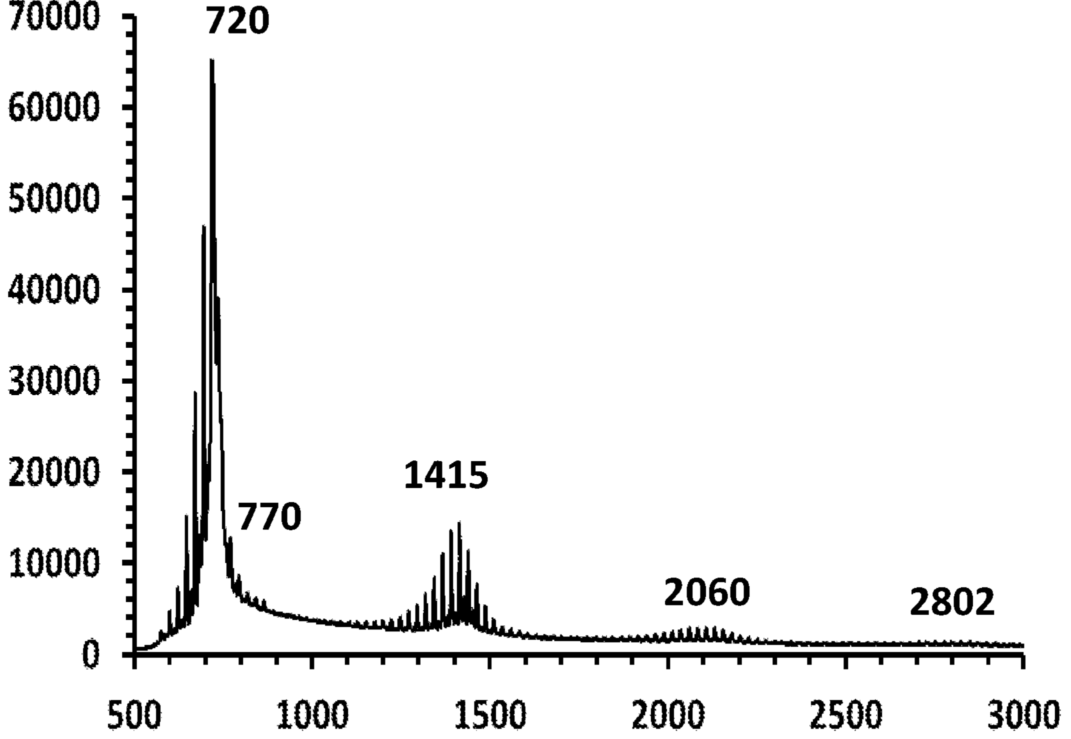
FIG. 24 is an illustration of experimental mass spectrograph data for C60-GSH.

FIG. 24 illustrates experimental data for the negative mode MALDI-TOF mass spectrograph of glutathione derivatized fullerene (C60), where the largest molecular peak at 720 mass-to-charge ratio represents the core molecule of C60. A molecular fragment of C60 fullerene plus some residual spallation fragment typically associated with a glutathione remnant is observed at a mass-to-charge of 770. The grouping of peaks at mass-to-charge ratio of 1415 represents the molecular fragments associated with one glutathione group functionalized to one fullerene molecule as the primary reaction product. The grouping of peaks at mass-to-charge ratio of 2060 represents the minor amounts of molecular fragments associated with two glutathione groups functionalized to one fullerene molecule. The grouping of peaks at mass-to-charge ratio of 2802 represents the trace amounts of molecular fragments associated with three glutathione groups functionalized to one fullerene molecule.

Figure 25:
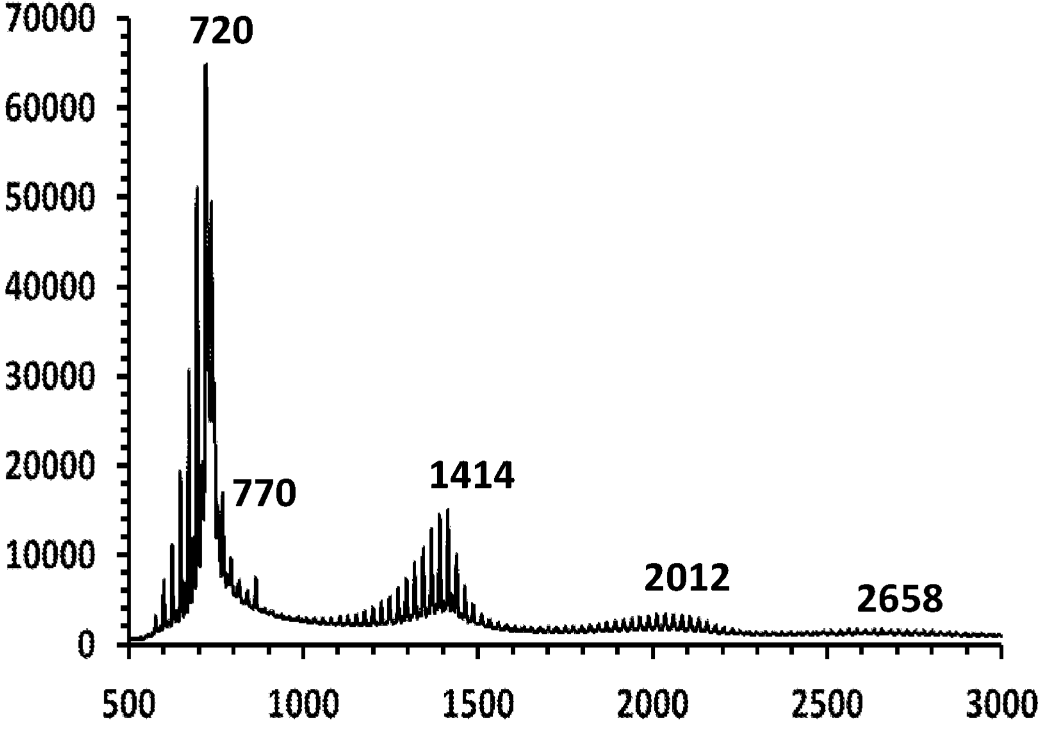
FIG. 25 is an illustration of experimental mass spectrograph data for a C60-GSH-ATP dual neurotransmitter nanoparticle ensemble.

FIG. 25 illustrates experimental mass spectrograph data for negative mode MALDI-TOF glutathione and adenosine triphosphate derivatized fullerene (C60), where the largest molecular peak at 720 mass-to-charge ratio represents the core molecule of C60. The trace peak at 770 mass-to-charge ratio indicates a partial glutathione fragment on the core fullerene molecule peak. The grouping of peaks at mass-to-charge ratio of 1414 represents the molecular fragments associated with one adenosine triphosphate group functionalized to one fullerene molecule, or one glutathione group functionalized to one fullerene, with significant overlap of spallation products for each functional moiety. The grouping of peaks at mass-to-charge ratio of 2012 represents the molecular fragments associated with one glutathione functional group and one adenosine triphosphate group where both functional groups chemically adduct to one fullerene molecule. The grouping of peaks at mass-to-charge ratio of

2658 represents the trace amounts of molecular fragments associated with three functional groups selected from one or two adenosine triphosphate groups with either two or one functionalized glutathione group, respectively, as reacted to one C60 fullerene molecule, being a C60-GSH-ATP dual neurotransmitter nanoparticle in accordance with these teachings.

As variations, combinations and modifications may be made in the construction and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments but defined in accordance with the foregoing claims appended hereto and their equivalents.

What is claimed is:

1. A method of treating autism spectrum disorders in a subject, comprising the step of:

administering to the subject an effective amount of a compound including a buckminsterfullerene C60 bonded to both a glutathione and an adenosine phosphate functional group.

2. The method of claim 1 wherein administering the compound comprises administering a composition containing the compound in a pharmaceutically acceptable carrier.

3. The method of claim 2 wherein the composition comprises a tablet, capsule, pill, powder, granule, or a form suitable for injection.

4. The method of claim 2 wherein administering the compound comprises administration by an intravenous, intramuscular, subcutaneous, intrathecal, intraperitoneal, topical, nasal, or oral route.

5. The method of claim 2 wherein an oral dosage comprises up to about 500 mg of the compound.

6. The method of claim 2 wherein administering the compound comprises intramuscular, intravenous, or subcutaneous administration in an amount of from about 0.1 mg/Kg to about 5 mg/Kg.

7. The method of claim 2 wherein administering the compound comprises administration by a nano aerosol, a vapor, a powder, a dust, or an aerosolized inhalant.

8. The method of claim 1 wherein the adenosine phosphate functional group comprises adenosine triphosphate.

9. A method of treating brain dysfunction in Alzheimer's disease in a subject, comprising the step of:

administering to the subject an effective amount of a compound including a buckminsterfullerene C60 bonded to both a glutathione and an adenosine phosphate functional group.

10. The method of claim 9 wherein administering the compound comprises administering a composition containing the compound in a pharmaceutically acceptable carrier.

11. The method of claim 10 wherein the composition comprises a tablet, capsule, pill, powder, granule, or a form suitable for injection.

12. The method of claim 10 wherein administering the compound comprises administration by an intravenous, intramuscular, subcutaneous, intrathecal, intraperitoneal, topical, nasal, or oral route.

13. The method of claim 10 wherein an oral dosage comprises up to about 500 mg of the compound.

14. The method of claim 10 wherein administering the compound comprises intramuscular, intravenous, or subcutaneous administration in an amount of from about 0.1 mg/Kg to about 5 mg/Kg.

15. The method of claim 10 wherein administering the compound comprises administration by a nano aerosol, a vapor, a powder, a dust, or an aerosolized inhalant.

16. The method of claim 9 wherein the adenosine phosphate functional group comprises adenosine triphosphate.

* * * * *